(12) United States Patent
Drera

(10) Patent No.: US 10,636,536 B1
(45) Date of Patent: Apr. 28, 2020

(54) SYSTEMS AND METHODS FOR PREPARING TAILORED RADIOACTIVE ISOTOPE SOLUTIONS

(71) Applicant: RADTRAN LLC, Centennial, CO (US)

(72) Inventor: Saleem S. Drera, Centennial, CO (US)

(73) Assignee: RADTRAN LLC, Centennial, CO (US)

( * ) Notice: Subject to any disclaimer, the term of this patent is extended or adjusted under 35 U.S.C. 154(b) by 0 days.

(21) Appl. No.: 15/895,267

(22) Filed: Feb. 13, 2018

Related U.S. Application Data

(60) Provisional application No. 62/458,418, filed on Feb. 13, 2017.

(51) Int. Cl.
    *G21G 1/00*      (2006.01)
    *A61K 51/00*      (2006.01)

(52) U.S. Cl.
    CPC ............ *G21G 1/001* (2013.01); *A61K 51/00* (2013.01); *G21G 2001/0089* (2013.01)

(58) Field of Classification Search
    CPC ................................ A61K 51/00; G21G 1/00
    See application file for complete search history.

(56) References Cited

U.S. PATENT DOCUMENTS

| | | | |
|---|---|---|---|
| 4,663,129 A | 5/1987 | Atcher et al. | |
| 5,863,439 A | 1/1999 | Dietz et al. | |
| 6,951,634 B2 * | 10/2005 | Tranter | C22B 60/0239 423/2 |
| 7,887,782 B2 * | 2/2011 | Schwarz | A61K 51/121 424/1.11 |
| 8,221,520 B2 | 7/2012 | Andreoletti et al. | |

OTHER PUBLICATIONS

Technical Data Sheet, "Empore™ Solid Phase Extraction Disks—RAD-Disks Strontium, Radium and Technetium," 3M Deutschland Gmbh, Neuss, Germany, 2009. (LIEMP113(EN)).
Technical Data Sheet, "Empore™ Radium RAD Disks—Method Summary: Test Method RA-195," 3M Company, Egan, Minnesota, 2009. (LITEMP018).
"Analytical methodology for the determination of Radium isotopes in environmental samples," International Atomic Energy Agency Analytical Quality in Nuclear Applications, pub. No. IAEA/AQ/19, Vienna, Austria, pp. 1-59, 2001.
"Rapid sampling using 3M membrane technology," Innovative Technology, Summary Report DOE/EM-0501, 29 pages, US Dept. of Energy, Office of Environmental Management, Office of Science and Technology, 2000.
Report: Technical Meeting on "Alpha emitting radionuclides and radiopharmaceuticals for therapy," Jun. 24-28, 2013, IAEA Headquarters, Vienna Austria, pp. 1-75.
Amer, S. I., "Simplified removal of chelated metals," *Metal Finishing*, 102(4):36-40, 2004.
Artun, Ozan, "Estimation of the production of medical Ac-225 on thorium material via proton accelerator," *Applied Radiation and Isotopes* 127:166-172, 2017.
Atcher, R. W., et al., "An improved generator for the production of $^{212}$Pb and $^{212}$Bi from $^{224}$Ra," *Applied Radiation and Isotopes* 39(4):283-286, 1988.
Atcher, R. W., et al., "A remote system for the separation of $^{228}$Th and $^{224}$Ra," *J. Radioanal. Nucl. Chem., Letters* 117(3):155-162, 1987.
Baidoo, K. E. et al., "Methodology for labeling proteins and peptide with lead-212 ($^{212}$Pb)," *Nuclear Medicine and Biology* 40:592-599, 2013.
Boldyrev, P. P., et al., "$^{212}$Pb/$^{212}$Bi generator for nuclear medicine," *Atomic Energy* 111(6):422-427, Apr. 2012.
Chen, Y., et al., "Separation of thorium and uranium in nitric acid solution using silica based anion exchange resin," Journal of Chromatography A 1466:37-41, 2016.
Chiarizia, R., et al., "Radium separation through complexation by aqueous crown ethers and extraction by dinonylnaphthalenesulfonic acid," *Reactive & Functional Polymers* 38:249-257, 1998.
Dietz, M. L., et al., "Effect of crown ethers on the ion-exchange behavior of alkaline earth metals toward improved ion-exchange methods for the separation and preconcentration of Radium," *Anal. Chem.* 69:3028-3037, 1997.
Fons-Castells, J., et al., "On the direct measurement of $^{226}$Ra and $^{228}$Ra using 3M Empore™ RAD disk by liquid scintillation spectrometry," *J. Radioanal. Nucl. Chem.* 309:1123-1131, 2016.
Griswold, J. R., et al., "Large scale accelerator production of $^{225}$Ac: Effective cross section for 78-192 MeV protons incident on $^{232}$Th targets," *Applied Radiation and Isotopes* 118:366-374, 2016.
Hassfjell, S. P., et al., "A generatoar for production of $^{212}$Pb and $^{212}$Bi," *Appl. Radiat. Isot.* 45(10):1021-1025, 1994.
Kasten, B. B., et al., "B7-H3-targeted $^{212}$Pb radioimmunotherapy of ovarian cancer in preclinical models," *Nuclear Medicine and Biology* 47:23-30, 2017.
Kasten, B. B., et al., "Imaging, biodistribution, and toxicology evaluation of $^{212}$Pb-TCMC-trastuzumab in nonhuman primates," *Nuclear Medicine and Biology* 43:391-396, 2016.
Kotovskii, A. A., et al., "Isolation of Radium-224," *Radiochemistry* 57(4):448-450, 2015.
Kuznetsov, R. A., et al., "A rapid method for radium regeneration from its sulfate," *Radiochemistry* 55(1):112-115, 2013.
Kuznetsov, R. A., et al., "Yields of activation products in $^{226}$Ra irradiation in the high-flux SM reactor," *Radiochemistry* 54(4):383-387, 2012.
Máthé, D., et al., "Production and in vivo imaging of $^{203}$Pb as a surrogate isotope for in vivo $^{212}$Pb internal absorbed dose studies," *Applied Radiation and Isotopes* 114:1-6, 2016.

(Continued)

*Primary Examiner* — Michael G. Hartley
*Assistant Examiner* — Jagadishwar R Samala
(74) *Attorney, Agent, or Firm* — Greenberg Traurig, LLP

(57) ABSTRACT

The present disclosure relates to systems and methods for producing tailored solutions or medicaments containing radioactive isotopes (e.g., alpha particle emitting radioactive isotopes). The solutions may be produced by appropriate aging and separation steps. Therapeutically effective amounts of Pb-212 and/or Bi-213 may thus be obtained.

11 Claims, 17 Drawing Sheets

(56) References Cited

OTHER PUBLICATIONS

Matyskin, A.V., et al., "Barium and Radium complexation with Ethylenediaminetetraacetic Acid in aqueous alkaline Sodium Chloride media," *J Solution Chem* 46:1951-1969, 2017.

Mobius, S., et al., "Extractive methods for fast radium analysis," *Advances in Liquid Scintillation Spectrometry*, Arizona Board of Regents on behalf of the University of Arizona, LSC, pp. 283-292, 2001.

Narbutt, J., et al., "Gamma Emitting Radiotracers $^{224}$Ra, $^{212}$Pb and $^{212}$Bi from Natural Thorium," *Applied Radiation and Isotopes* 49(1-2):89-91, 1998.

Odo, U., et al., "Acute promyelocytic leukemia after treatment of metastatic castration-resistant prostate cancer with Radium-223," *Clinical Genitourinary Cancer*, 15(3): e501-e502, 2017.

Scarpitta, S. C., et al., "Evaluation of 3M Empore™ Rad disks for radium determination in water," US Dept. of Energy, Environmental Measurements Laboratory, 42$^d$ Annual Conference on bioassay, Analytical and Environmental Radiochemistry, San Francisco, CA, Oct. 13-17, 1996.

Song, L., et al., "Rapid determination of radium-224/226 in seawater sample by alpha spectrometry," *Journal of Environmental Radioactivity* 171:169-175, 2017.

Su, Fu-Min, et al., "Pretargeted radioimmunotherapy in tumored mice using an in vivo $^{212}$Pb/$^{212}$Bi generator," *Nuclear Medicine and Biology* 32:741-747, 2005.

Weidner, J.W., et al., "Proton-induced cross sections relevant to production of $^{225}$Ac and $^{223}$Ra in natural thorium targets below 200 MeV," *Applied Radiation and Isotopes* 70:2602-2607, 2012.

Westrom, S., et al., "Preparation of $^{212}$Pb-labeled monoclonal antibody using a novel $^{224}$Ra-Base generator solution," *Nuclear Medicine and Biology* 51:1-9, 2017.

Wrasidlo, W., et al., "Generation of lead-212 and radioimmunoconjugates for use in cancer therapy and the 'emanating power' of stearates," *Colloids and Surfaces A: Physicochemical and Engineering Aspects* 186:123-128, 2001.

Yong, K., et al., "Application of 212Pb for targeted α-particle therapy (TAT): pre-clinical and mechanistic understanding through to clinical translation," *AIMS Med Sci.* 2(3):228-245, 2015.

Zucchini, G. L., et al., "Isotopic Generator for $^{212}$Pb and $^{212}$Bi," *Int. J. Nucl. Med. Biol.* 9:83-84, 1982.

* cited by examiner

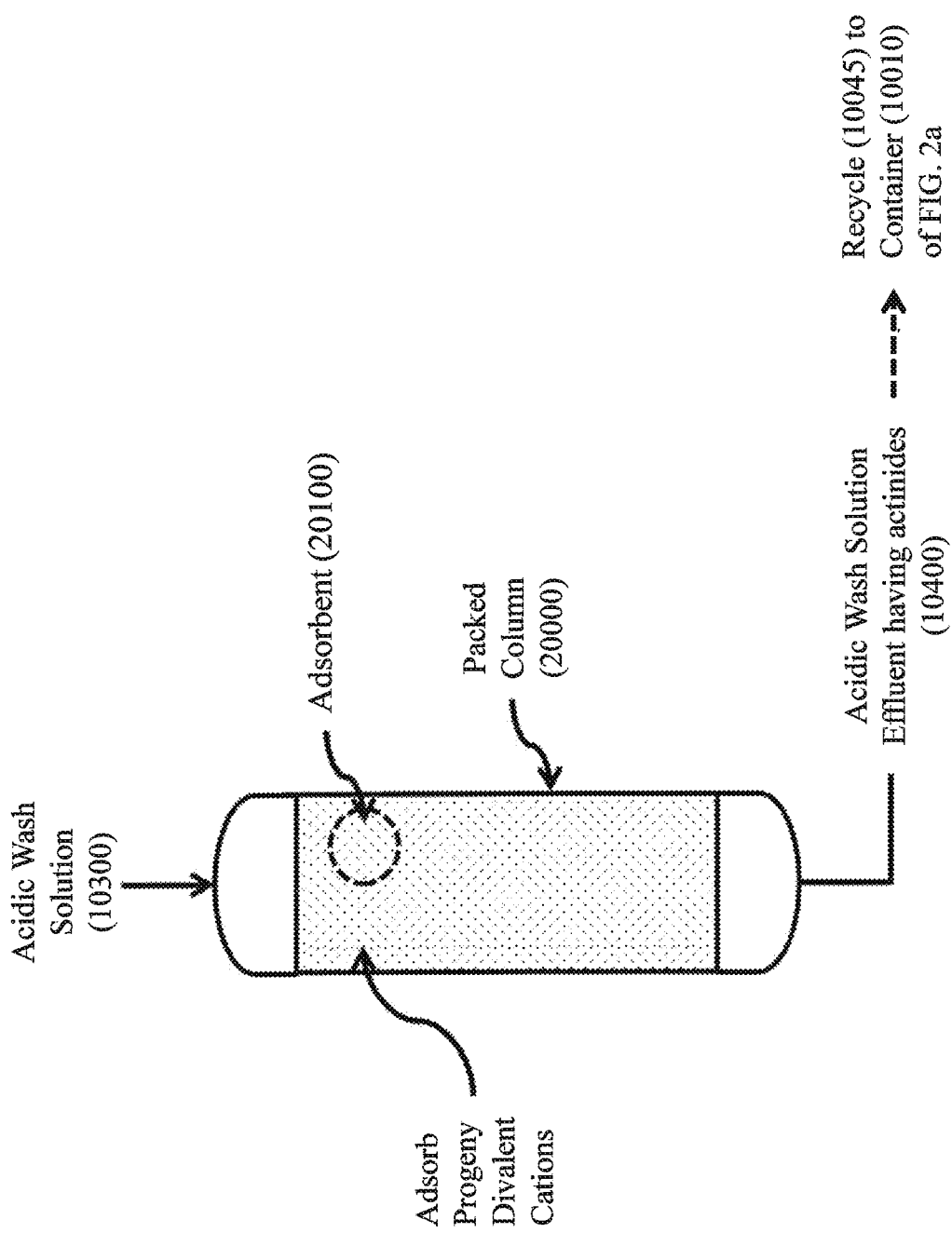

SYSTEMS AND METHODS FOR PREPARING TAILORED RADIOACTIVE ISOTOPE SOLUTIONS

CROSS-REFERENCE TO RELATED APPLICATION

This application claims the benefit of priority of U.S. Provisional Patent Application No. 62/458,418, filed Feb. 13, 2017, entitled "SYSTEMS AND METHODS FOR PREPARING Ra228, Th228 AND/OR Ra224" which is incorporated herein by reference in its entirety.

BACKGROUND

In May 2013, the Food and Drug Administration (FDA) approved the first cancer treatment drug containing an alpha-emitting isotope. Pb-212 and Bi-213 are known alpha-emitting isotopes potentially useful for this purpose. See, e.g., Yong, K. et al., "Application of 212Pb for Targeted α-particle Therapy (TAT): Pre-clinical and Mechanistic Understanding through to Clinical Translation," AIMS Med Sci. 2015; 2(3): 228-245, published online 2015 Aug. 18. doi: 10.3934/medsci.2015.3.228; and Dekempeneer, Y. et al., "Targeted alpha therapy using short-lived alpha-particles and the promise of nanobodies as targeting vehicle," Expert Opin Biol Ther. 2016 Aug. 2; 16(8): 1035-1047, published online 2016 May 19. doi: 10.1080/14712598.2016.1185412.

SUMMARY OF THE DISCLOSURE

Broadly, the present patent application relates to methods of producing radioactive isotopes and useful solutions or medicaments containing such radioactive isotopes. In one embodiment, the radioactive isotopes are alpha particle emitting radioactive isotopes ("APERI"). Such APERI may be generated from APERI generator elements or "generators". Useful APERI generators are described in further detail below. Using appropriate separation materials (e.g., adsorbents, such as macrocyclic polyether materials), sequences, extraction solutions and/or washes, APERI elements (e.g., APERI cations) may be separated from other materials. Accordingly, APERI-rich effluents may be produced. Such APERI-rich effluents may be used in appropriate therapies, such as cancer therapies. In one embodiment, an APERI-rich effluent is used in targeted alpha therapy or "TAT". In one embodiment, APERI of an APERI-rich effluent are attached to one or more antibodies. At least some of the antibodies may be injected into a human to facilitate TAT.

In one approach, a method for producing APERI-containing solutions and/or APERI-containing medicaments includes aging a starting actinide element solution, the starting actinide element solution comprise an APERI generator (e.g., Th-232, U-233, Th-229). The APERI generator may be in ionic form in the starting actinide element solution. The starting actinide element solution, therefore, generally contains APERI-generator cations. Due to the aging, at least some of the APERI generator cations radioactively decay, and this radioactive decay results in the production progeny divalent cations. In the case of a Th-232 decay chain, the divalent cations may be Ra-228 cations, Ra-224 cations, and Pb cations (e.g., Pb-212; Pb-208)). In the case of a U-233 decay chain, the divalent cations may be Ra-225 cations and Pb-209 cations. Hence, the aging of the starting actinide element solution generally results in the production of an aged starting actinide element solution comprising progeny divalent cations.

After or concomitant to the aging step, the progeny divalent cations may be separated from the non-divalent ions of the aged starting actinide element solution. In one embodiment, a separating step may include exposing the aged starting actinide element solution to an adsorbent, wherein at least some of the progeny divalent cations are adsorbed (e.g., selectively adsorbed) by the adsorbent. In one embodiment, the adsorbent comprises one or more macrocyclic polyether materials. In one embodiment, a macrocyclic polyether material is a crown ether. Due to the adsorbing, at least some of the progeny divalent cations may be removed from the aged actinide element solution, thereby creating a depleted aged starting actinide element solution. This depleted solution may be recycled and reused as the starting actinide element solution. In the case of a Th-232 decay chain, the adsorbed progeny divalent cations may be Ra-228, Ra-224, Pb-212, and Pb-208. In the case of a U-233 decay chain, the adsorbed divalent cations may be Ra-225 and Pb-209. In some embodiments, an adsorbent wash may be used before and/or after a separation step (e.g., to further remove residual non-divalent cation materials). The adsorbent wash may comprise contacting the adsorbent with an acidic solution.

After the separating step, the progeny divalent cations may be retrieved (e.g., in the case of a Th-232 decay chain), or the progeny divalent cations may be allowed to further age, while adsorbed to the adsorbent, into non-divalent cations (e.g., in the case of a U-233 decay chain), which are subsequently retrieved by washing with an appropriate wash solution.

In one embodiment, adsorbed divalent cations are retrieved via an extraction solution (e.g., EDTA), wherein the adsorbent comprising the adsorbed progeny divalent cations is contacted by the extraction solution. This particular embodiment may be more efficient for the Th-232 decay chain materials. In any case, due to the contacting, at least some of the progeny divalent cations (e.g., Ra-228, Ra-225, Ra-224, Pb-212, Pb-208) may be desorbed from the adsorbent. Accordingly, an extraction effluent solution may be recovered, and with the extraction effluent solution comprising at least some progeny divalent cations therein. In one embodiment, at least half of the adsorbed progeny divalent cations are recovered in the extraction solution. In another embodiment, at least 75% of the adsorbed progeny divalent cations are recovered in the extraction solution. In another embodiment, at least 90% of the adsorbed progeny divalent cations are recovered in the extraction solution. In one embodiment, the extraction comprises producing coordination bonds between the extraction solution and the progeny divalent cations. In one embodiment, the producing coordination bonds step comprises chelating or chelation. In some embodiments, an acidic wash may be used before and/or after an extraction, such as to further remove residual non-divalent cation materials.

After the retrieving step, the extraction effluent solution may be aged, where at least some of the progeny divalent cations radioactively decay, thereby producing an aged extraction effluent solution. In one embodiment, the extraction effluent solution is acidified during or concomitant to its aging. The acidifying may facilitate removal of the coordination bonds (e.g., the breaking-of) between the extraction solution and the progeny divalent cations (aged or unaged). Due to this aging step, intermediate non-divalent APERI generators may be produced (e.g., Ac-228; Th-228). The intermediate non-divalent APERI generators may be in ionic form in the aged extraction effluent solution. In one embodiment, the APERI generators may be in cationic form (e.g., in the form of Ac-228 cations; in the form of Th-228 cations). The aged extraction effluent solution generally also includes at least some of the progeny divalent cations.

The ionic products of the aged extraction effluent solution may be separated. For instance, after or concomitant to the aging of the extraction effluent, the progeny divalent cations (e.g., Ra-228, Ra-224, Pb-212, Pb-208) may be separated from non-divalent ions (e.g., Ac-228, Th-228) of the aged extraction effluent solution. In one embodiment, a separating step may include exposing the aged extraction effluent solution to an adsorbent, wherein at least some of the progeny divalent cations are adsorbed (e.g., selectively adsorbed) by the adsorbent, which adsorbent may be the same as, or may be different from, the adsorbent used above with respect to the aged starting actinide element solution. In one embodiment, the adsorbent comprises one or more macrocyclic polyether materials, which macrocyclic polyether materials may be the same as, or different from, any macrocyclic polyether materials used above with respect to the aged starting actinide element solution. In one embodiment, the adsorbent comprises one or more crown ethers, which crown ether(s) may be the same as, or different from, any crown ether(s) used above with respect to the aged starting actinide element solution.

Due to the adsorbing, at least some of the progeny divalent cations may be removed from the aged extraction effluent solution. The non-divalent cations may be discharged in the form of a non-divalent effluent (e.g., a purified thorium effluent) and recovered. In one embodiment, the non-divalent effluent may include Th-228 and/or Ac-228, among others (e.g., when the APERI generator is Th-232). In one embodiment, the effluent contains appreciable an amount of Th-228 and is thus considered a purified thorium-containing effluent. In one embodiment, this purified thorium effluent is provided to a medical entity (e.g., a hospital; a doctor; a drug manufacturer) for subsequent use. The medical entity may, for instance, and as described in further detail below, allow the purified thorium effluent to age to produce Pb-212 cations, which Pb-212 cations may subsequently be attached to a carrier (e.g., an antibody; a targeting molecule) for use in TAT or other applicable therapies. For instance, the Pb-212 attached to the carrier may be injected into a human.

In one embodiment, the non-divalent effluent is further refined. For instance, a purified thorium effluent may be aged to produce an Ra-224-containing solution, where at least some of the Th-228 cations are held for a time sufficient to radioactively decay into divalent Ra-224 cations, thereby producing an aged Ra-224-containing solution. Further separation operations may be utilized relative to the aged Ra-224-containing solution, where divalent cations are separated from non-divalent cations (e.g., using a suitable adsorbent, as described above). In one embodiment, the Ra-224 cations are removed from the Ra-224-containing solution via an applicable adsorbent and an enriched thorium-containing effluent is discharged and recovered. In one embodiment, the adsorbent comprises one or more macrocyclic polyether materials, which macrocyclic polyether materials may be the same as, or different from, any macrocyclic polyether materials used above with respect to the aged starting actinide element solution and/or the aged extraction effluent solution. In one embodiment, the adsorbent comprises one or more crown ethers, which crown ether(s) may be the same as, or different from, any crown ether(s) used above with respect to the aged starting actinide element solution and/or the aged extraction effluent solution. The enriched thorium-containing effluent may be recycled and reused as the purified thorium effluent.

Similarly to the prior retrieval step, described above, the divalent cations of the Ra-224-containing solution may be retrieved. In one embodiment, an extraction solution (e.g., EDTA) is used to extract the progeny divalent cations (e.g., Ra-224), wherein the adsorbent comprising the adsorbed progeny divalent cations is contacted by the extraction solution. Due to the contacting, at least some of the progeny divalent cations may be desorbed from the adsorbent. Accordingly, an Ra-224-rich effluent may be recovered, the Ra-224-rich effluent comprising high concentration of Ra-224 cations relative to the prior solutions. In one embodiment, at least half of the adsorbed Ra-224 cations are recovered in the extraction solution. In another embodiment, at least 75% of the Ra-224 divalent cations are recovered in the extraction solution. In another embodiment, at least 90% of the Ra-224 divalent cations are recovered in the extraction solution. In one embodiment, the extraction comprises producing coordination bonds between the extraction solution and the Ra-224 cations. In one embodiment, the producing coordination bonds step comprises chelating or chelation. In one embodiment, the effluent contains appreciable amount of Ra-224 cations. In one embodiment, the Ra-224-rich effluent is provided to a medical entity (e.g., a hospital; a doctor; a drug manufacturer) for subsequent use. The medical entity may, for instance, and as described in further detail below, allow the Ra-224-rich effluent to age to produce Pb-212 cations, which Pb-212 cations may subsequently be attached to a carrier (e.g., an antibody; a targeting molecule) for use in TAT or other applicable therapies. For instance, the Pb-212 attached to the carrier may be injected into a human.

As noted above, the adsorbed divalent cations may be aged into non-divalent cations. This particular embodiment may be more efficient for the U-233 decay chain materials, and is discussed in greater detail below. In any case, due to the aging, progeny non-divalent materials may be produced via radioactive decay (e.g., the radioactive decay of Ra-225 cations into Ac-225 cations). Thus, an aged adsorbent may be produced, the aged adsorbent having non-divalent cations (e.g., Ac-225 cations). A method may include contacting the aged adsorbent with a wash solution (e.g., an acidic wash solution), thereby removing at least some of the progeny non-divalent cations from the aged adsorbent. This aging and washing may be completed repeatedly, as necessary, to produce applicable wash solutions having non-divalent cations therein. In one embodiment, an Ac-225-containing effluent is produced. In one embodiment, an Ac-225-containing effluent is used as an intermediate APERI for the generation of Bi-213. In one embodiment, a Bi-213-containing solution is produced from due to radioactive decay of the Ac-225 cations of the Ac-225 containing effluent. In one embodiment, a Ac-225-containing effluent is provided to a medical entity (e.g., a hospital; a doctor; a drug manufacturer) for subsequent use. The medical entity may, for instance, and as described in further detail below, allow the Ac-225-containing effluent to age to produce Bi-213 cations, which Bi-213 cations may subsequently be attached to a carrier (e.g., an antibody; a targeting molecule) for use in TAT or other applicable therapies. For instance, the Bi-213 attached to the carrier may be injected into a human.

One or more of the above effluents and/or wash solutions may comprises some levels of the adsorbents. For instance, any of the extraction effluent solution, the non-divalent effluent (e.g., the purified thorium effluent), the Ra-224-rich effluent, the Ac-225-containing effluent, or other effluents or wash solutions may comprise adsorbent materials therein (e.g., macrocyclic polyether materials, such as one or more crown ether materials). In one embodiment, an effluent or wash solution comprises at least 0.01 ppm of adsorbent. In another embodiment, an effluent or wash solution comprises 0.1 ppm of adsorbent. In yet another embodiment, an effluent or wash solution comprises 0.5 ppm of adsorbent. In another embodiment, an effluent or wash solution comprises 1 ppm of adsorbent. In yet another embodiment, an effluent or wash solution comprises 5 ppm of adsorbent. In yet another embodiment, an effluent or wash solution comprises 10 ppm of adsorbent. In one embodiment, an effluent or wash solution comprises not greater than 1000 ppm of adsorbent. In another embodiment, an effluent or wash solution comprises not greater than 500 ppm of adsorbent.

While the above-described methods steps have been described as a series of operations, it is anticipated that, with appropriate volumes, some of the steps may be carried out in parallel. Further, many of the individual method steps have separate utility, and are inventive of their own right. Further, these and other aspects, advantages, and novel features of the invention are set forth in part in the description that follows and will become apparent to those skilled in the art upon examination of the following description and figures, or may be learned by practicing the invention.

BRIEF DESCRIPTION OF THE DRAWINGS

FIG. 2c is a schematic diagram of an embodiment for contacting an adsorbent with an acidic wash solution.

DETAILED DESCRIPTION

The present disclosure relates to systems and methods for producing solutions comprising alpha particle emitting radioactive isotopes. Such alpha particle emitting radioactive isotopes may be useful in targeted alpha therapy ("TAT"). For instance, targeted alpha therapy cancer treatments may be used in radioimmunotherapy methods. In this regard, the methods and products described herein generally relate to alpha particle emitting radioactive isotopes and elements capable of generating such alpha particle emitting radioactive isotopes via radioactive decay. Elements capable of generating alpha particle emitting radioactive isotopes via radioactive decay are sometimes referred to herein as "generators".

One useful alpha particle emitting isotope is Pb-212, which may be generated via radioactive decay of one or more of Ra-224, Ra-228, and Th-228. Another useful alpha particle emitting isotope is Bi-213, which may be produced via radioactive decay of one or more of Ac-225 and Ra-225. Ac-225 may itself be a useful alpha particle emitting radioactive isotope.

i. Methods

As noted above, broadly, the present disclosure relates to systems and methods for producing solutions comprising alpha particle emitting isotopes and generators thereof. For instance, the methods described herein may be useful in producing solutions comprising therapeutic amounts of alpha emitting particle isotopes Pb-212, Bi-213, and Ac-225. Furthermore, the methods described herein may be useful in producing solutions comprising therapeutic amounts of Ra-228, Th-228, and/or Ra-224, any of which may be used to generate Pb-212. Additionally, the methods described herein may be useful in producing solutions comprising therapeutic amounts of Ac-225, and/or Ra-225, either of which may be used to generate Bi-213. In another aspect, Ac-225 itself may be used as an alpha particle emitting radioactive isotope. In this regard, Ac-225 may decay via three subsequent alpha particle emissions to Bi-213, which itself will undergo a fourth alpha particle emission to Pb-209. The methods described herein generally employ an appropriate precursor material (generator) with appropriate aging (e.g., radioactive decay), and separation steps to produce quantities of alpha particle emitting radioactive isotopes (e.g., U-233; Th-232; Th-229). For instance, radioactive isotopes capable of generating Pb-212, such as Ra-228, Th-228, and Ra-224, may be produced via the methods described herein from a Th-232 precursor material. In another example, radioactive isotopes capable of generating Bi-213, such as Ac-225 and Ra-225, may be produced via the methods described herein from a U-233 and/or Th-229 precursor material.

Methods Utilizing Th-232 as a Precursor

Figure 1A:
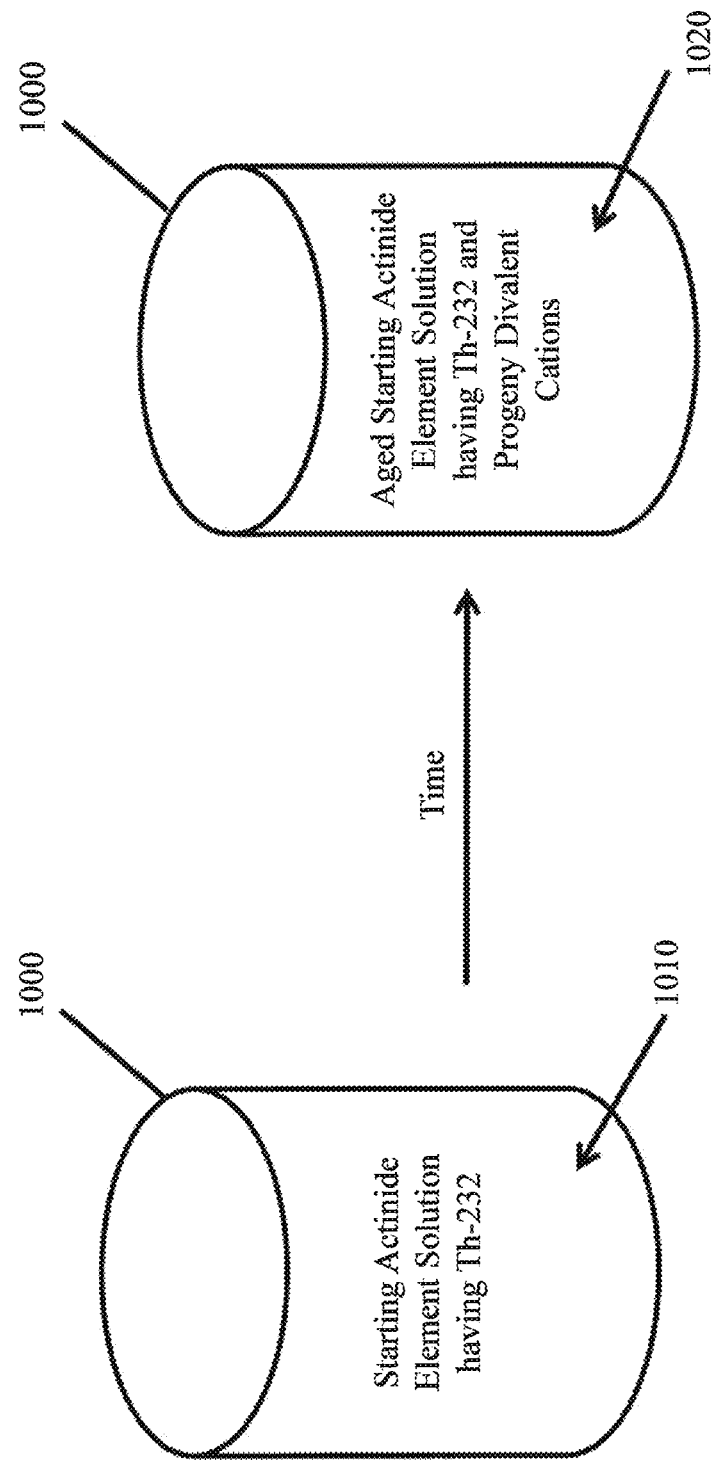
FIG. 1a is a schematic diagram of an embodiment for aging a starting actinide element solution having Th-232 therein.

In one approach, and now with reference to FIG. 1a, Th-232 may be used as a precursor for the production of the radioactive isotopes Ra-228, Th-228, and/or Ra-224. Such product solutions comprising one or more of Ra-228, Th-228, and/or Ra-224 may be suitable for generating Pb-212. In the illustrated embodiment, a starting actinide element solution (1010) comprising at least some Th-232 may be aged. In general, the starting actinide element solution is an acidic solution comprising Th-232 cations.

The starting actinide element solution may be produced via acidification of a Th-232 material, or may be produced by dissolution of a Th-232 salt (e.g., Th-232 nitrate). Due to the aging (e.g., radioactive decay of Th-232 and/or progeny elements), an aged starting actinide element solution having progeny divalent cations (1020) may be produced. The progeny divalent cations (defined below) produced via the radioactive decay of Th-232 may include one or more of Ra-228, Ra-224, Pb-212, and Pb-208. The starting actinide element solution (1010) and the subsequent aged starting actinide element solution (1020) may be held in a suitable container (1000), such as those described in greater detail below.

As used herein, "divalent cations" means an element having a charge of +2. Non-limiting examples of divalent cations include radium isotopes and lead isotopes, among others.

As used herein, "progeny" means one or more elements produced as a result of radioactive decay of a prior element. For instance, the progeny of element Th-232 include Ra-228, Ac-228, Th-228, Ra-224, Rn-220, Po-216, Pb-212, Bi-212, Po-212, Tl-208, and Pb-208.

As used herein, a "progeny cation" is a cation produced as a result of radioactive decay of a prior cation. For instance, a Th-232 tetravalent (+4) cation may decay into a Ra-228 divalent (+2) cation via emission of an alpha particle. In this scenario, the progeny cation is the Ra-228 divalent cation.

As used herein, "a progeny divalent cation" is a divalent cation produced as a result of radioactive decay of a prior cation.

Figure 1B:
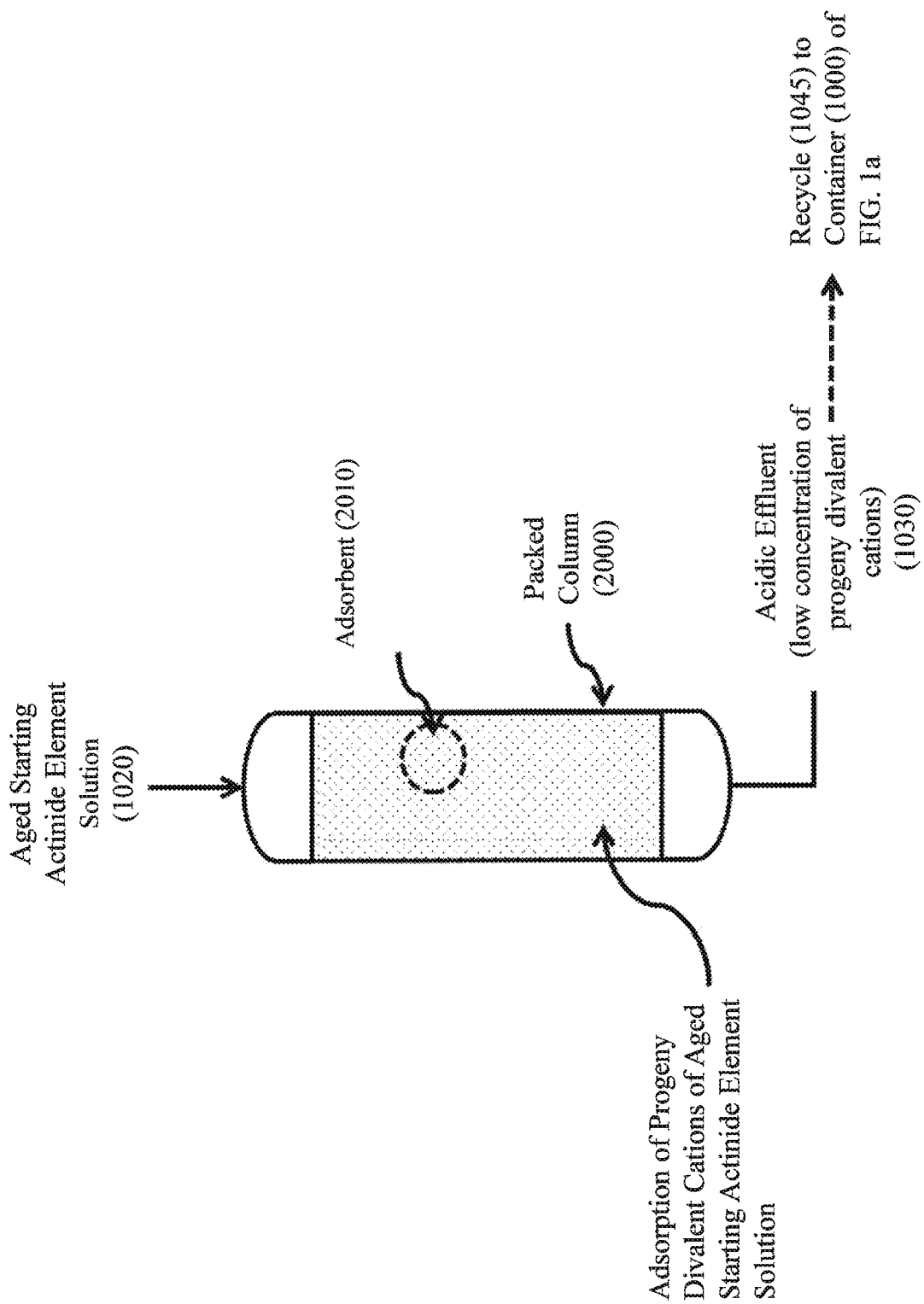
FIG. 1b is a schematic diagram of an embodiment for exposing an aged starting actinide element solution to an adsorbent.

Now with reference to FIG. 1b, in the illustrated embodiment the aged starting actinide element solution (1020) may be exposed to an adsorbent (2010). In this regard, one such suitable method for exposing the aged starting actinide element solution (1020) includes the use of a packed column (2000) comprising the adsorbent (2010). The adsorbent (2010) may have a selectivity towards divalent cations, and accordingly, may adsorb at least some progeny divalent cations of the aged starting actinide element solution (1020). Suitable adsorbents (2010) having a selectivity towards divalent cations are discussed in greater detail below. Following exposure of the aged starting actinide element solution (1020) to the adsorbent (2010), an acidic effluent (1030) may be recovered. The acidic effluent (1030) generally has a lower concentration of progeny divalent cations as compared to the aged starting actinide element solution (1020). The acidic effluent (1030) may be recycled (1045) to the container (1000) for subsequent aging. Also, the acidic effluent (1030) may itself be a starting actinide element solution (1010), which is aged to produce an aged starting actinide element solution (1020). The starting actinide element solution (1020) may be iteratively aged to an aged starting actinide element solution (1020), contacted with an adsorbent (2010), and recycled (1045). Due to the relatively large half-life of Th-232 of approximately 14 billion years, the process may be repeated indefinitely.

As used herein, as "adsorbent" is a material that adsorbs another material. "Adsorb" and the like means to adhere to the surface of an adsorbent, such as by chemical, physical and/or electrical attraction. An adsorbed material is a material that adheres to the surface of an adsorbent due to adsorption. An adsorbed material may be removed from the surface of the adsorbent, for instance, by an appropriate solvent and/or an appropriate solution (e.g., an extraction solution) having an appropriate pH, i.e., a solvent/solution may desorb an adsorbed material (e.g., a divalent cation) from the adsorbent (e.g., a crown ether material). In another aspect, the surface may include molecules (e.g., a crown ether) tethered (e.g., via chemical bonding) to the surface of an adsorbent, and such molecules are considered as being a part of the surface herein.

Figure 1C:
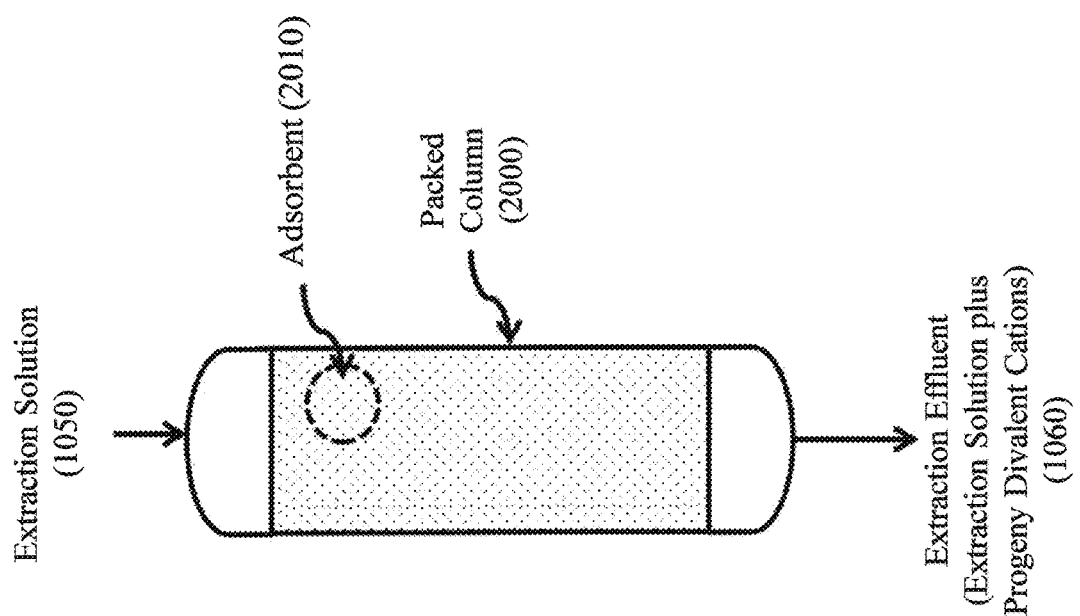
FIG. 1c is a schematic diagram of an embodiment for contacting an adsorbent with an extraction solution.

With reference now to FIG. 1c, the adsorbent (2010) may be contacted with an extraction solution (1050). Suitable extraction solutions (sometimes called extraction agents herein) are discussed in greater detail below. In this regard, the extraction solution is generally suitable for extracting at least some of adsorbed the progeny divalent cations from the adsorbent (2010). Following contact of the adsorbent (2010) with the extraction solution (1050), an extraction effluent (1060) comprising the extraction solution (1050) and at least some progeny divalent cations may be discharged from the packed column (2000) and recovered.

In an alternative approach (not depicted), the adsorbent (2010) may be aged, thereby radioactively decaying at least some of the adsorbed progeny divalent cations. In this regard, aging the adsorbent (2010) may produce at least some Th-228 cations within the adsorbent (2010). The adsorbent (2010) comprising the Th-228 cations may be contacted with an acidic wash solution, thereby transferring at least some of the Th-228 cations of the adsorbent (2010) into the acidic wash solution. A Th-228 acidic effluent comprising at least some Th-228 cations may then be discharged and recovered. For instance, the Th-228 acidic effluent may be discharged from the packed column (2000). The Th-228 acidic effluent comprising the Th-228 cations may be used to generate Pb-212.

Figure 1D:
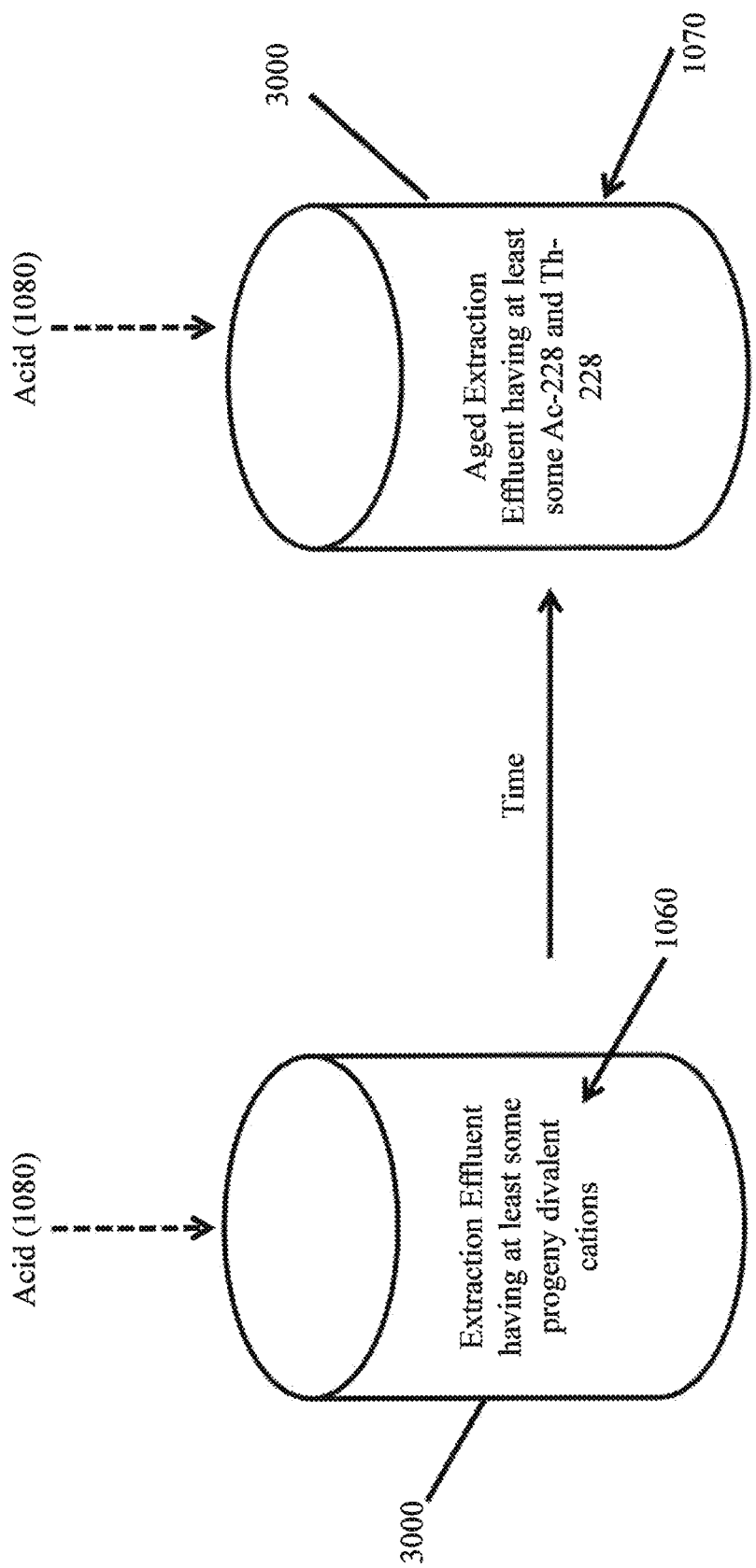
FIG. 1d is a schematic diagram of an embodiment for aging an extraction effluent.
Figure 1E:
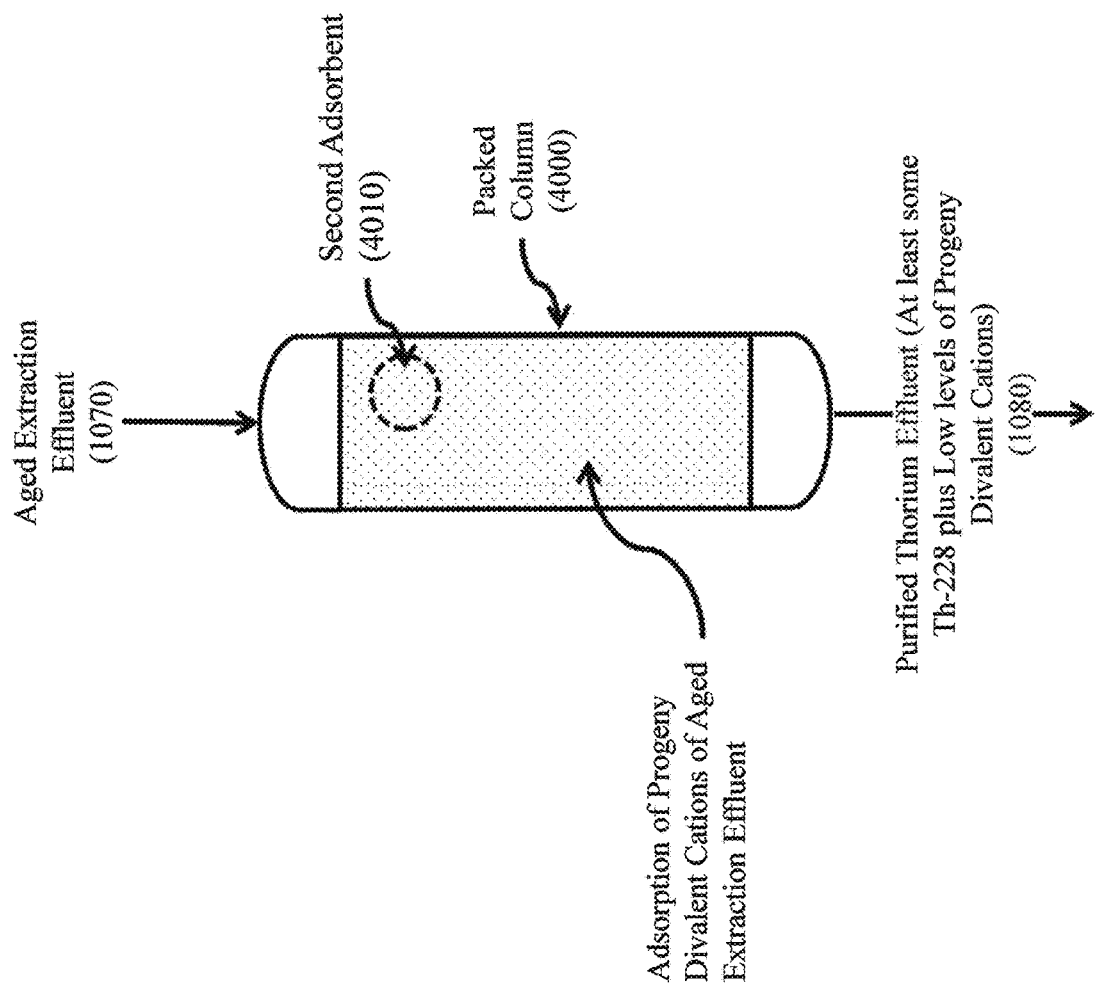
FIG. 1e is a schematic diagram of an embodiment for exposing an aged extraction effluent to a second adsorbent.

With reference now to FIG. 1d, the extraction effluent (1060) may optionally be acidified with an acid (1080). With or without acidifying, the extraction effluent (1060) may also be aged, where at least some of the progeny divalent cations radioactively decay. In this regard, the aging may result in the production of at least some Ac-228 cations and Th-228 cations generated from the progeny divalent cations. Due to the aging step the aged extraction effluent (1070) generally includes at least some progeny divalent cations. An aged extraction effluent (1070) comprising at least some Ac-228 cations and Th-228 cations may be discharged and recovered. The aged extraction effluent (1070) may also be acidified by the addition of acid (1080). The acidification may facilitate removal of the coordination bonds (e.g., the breaking-of) between the extraction solution and the progeny divalent cations. In one embodiment, an extraction effluent comprising EDTA is acidified via the addition of nitric acid. Regardless, at least one of the extraction effluent (1060) or aged extraction effluent (1070), may be acidified prior to exposing the aged extraction effluent (1070) to a second adsorbent (as shown in FIG. 1e). The extraction effluent (1060) may also be acidified at any time during the aging. Due to the aging step, the aged extraction effluent (1070) generally includes at least some progeny divalent cations generated from the progeny divalent cations. As noted in FIG. 1d, the extraction effluent (1060) and aged extraction effluent (1070) may be held within a suitable container (3000), as discussed in greater detail below.

With reference now to FIG. 1e, the aged extraction effluent (1070) may be exposed to a second adsorbent (4010). One suitable method for exposing the aged extraction effluent (1070) to the adsorbent (4010) may include exposing the aged extraction effluent (1070) to a packed column (4000) comprising the second adsorbent (4010), as illustrated. As noted above, the aged extraction effluent (1070) may include at least some progeny divalent cations. Further, the adsorbent (4010) may have a selectivity towards divalent cations, and, accordingly, may adsorb at least some of the progeny divalent cations of the aged extraction effluent (1070). After exposing the aged extraction effluent (1070) to the second adsorbent (4010), a purified thorium effluent (1080) having at least some Th-228 may be discharged from the packed column (4000) and recovered. The purified thorium effluent (1080) generally comprises lower amounts of progeny divalent cations relative to the aged extraction effluent (1070). In some embodiments, the purified thorium effluent (1080) may comprise some Ac-228 cations. However, due to short half-life of Ac-228 (approximately 6.1 minutes), most of the Ac-228 cations may radioactively decay to Th-228 cations. The purified thorium effluent (1080) comprising the Th-228 cations may be a suitable product for generating Pb-212.

Figure 1F:
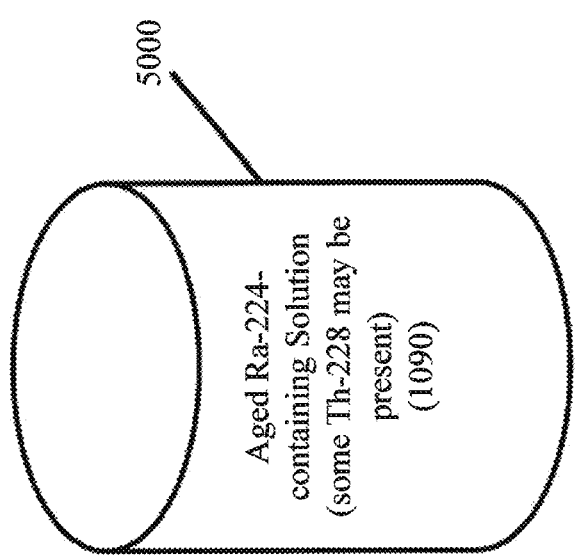
FIG. 1f is a schematic diagram of an embodiment for aging a purified thorium effluent.
Figure 1F:
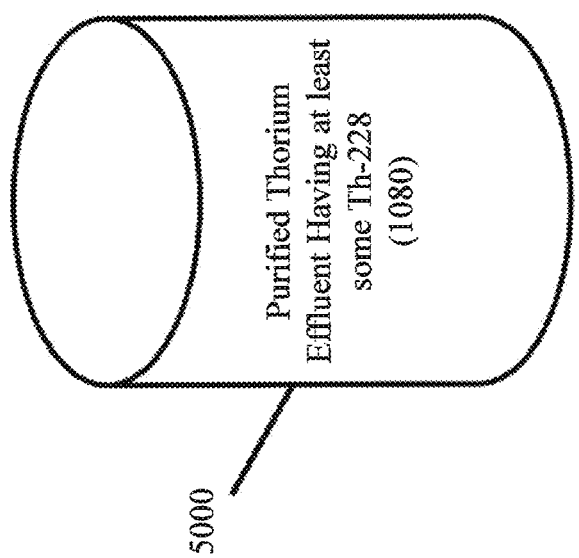

With reference now to FIG. 1f, the purified thorium effluent (1080) may be aged and at least some of the Th-228 cations of the purified thorium effluent (1080) may radioactively decay to produce Ra-224 cations. Thus, aging the purified thorium effluent (1080) may produce a Ra-224-containing solution (1090). As noted in FIG. 1f, the purified thorium effluent (1080) and the aged Ra-224-containing solution (1090) may be held within a suitable container (5000), as discussed in greater detail below.

Figure 1G:
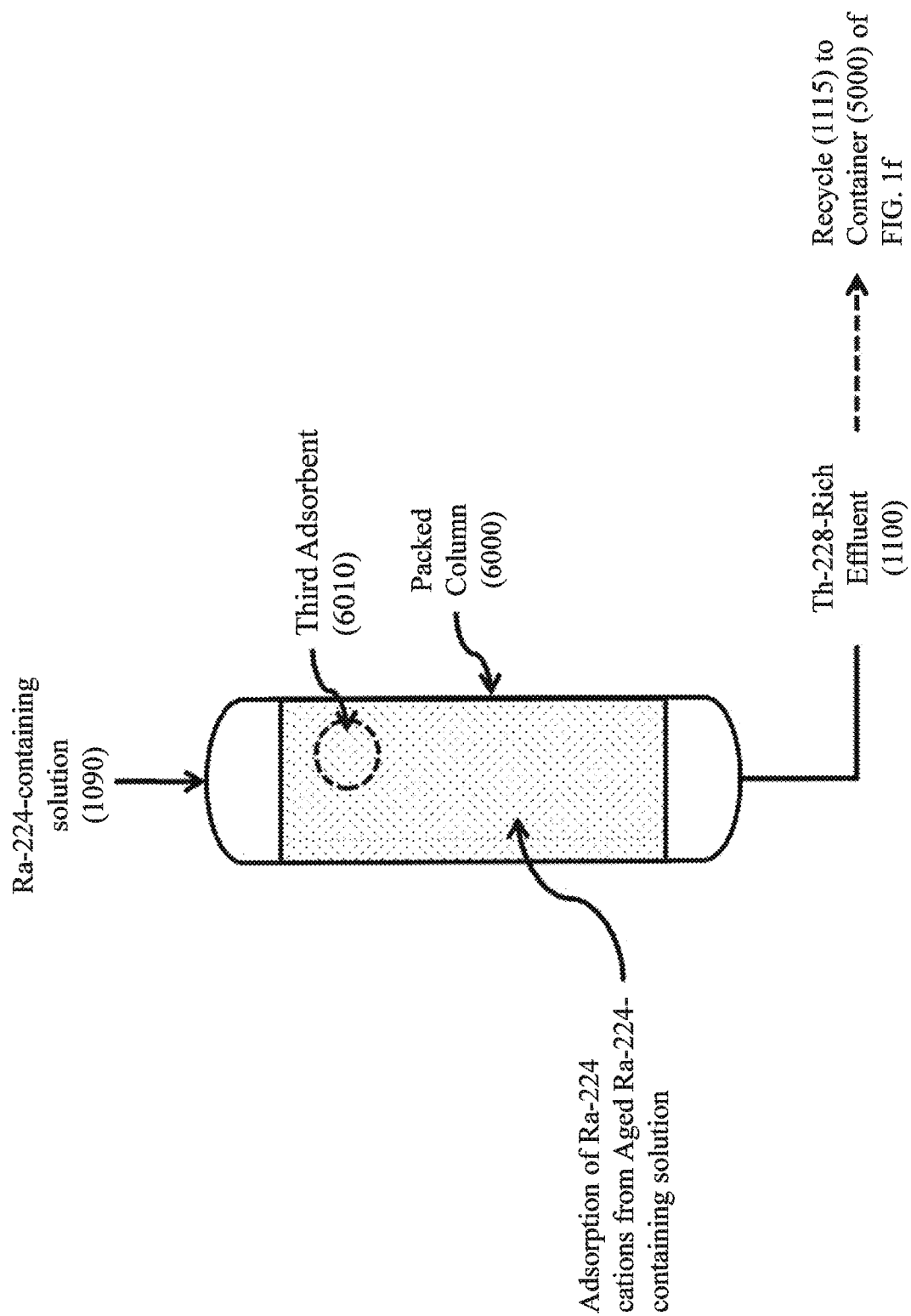
FIG. 1g is a schematic diagram of an embodiment for exposing an Ra-224 containing solution to an adsorbent.

With reference now to FIG. 1g, the Ra-224-containing solution (1090) may be contacted with a third adsorbent (6010). The third adsorbent may have a selectivity toward divalent cations (e.g., Ra-224 cations). Thus, during the contacting, at least some of the Ra-224 cations of the Ra-224-containing solution may be adsorbed by the third adsorbent (6010). One such suitable method for exposing the Ra-224-containing solution (1090) to the third adsorbent (6010) includes exposing the Ra-224-containing solution to a packed column (6000) comprising the third adsorbent (6010), as illustrated. A Th-228-rich effluent (1100) may be discharged from the packed column (6000) and recovered. In some embodiments, at least some of the Th-228-rich effluent may be recycled (1115) to the container (5000) shown in FIG. 1f for subsequent aging and production of subsequent Ra-224-containing solutions. Thus, the purified thorium effluent (1080) may be iteratively aged to produce Ra-224-containing solution (1090), contacted with the third adsorbent (6010) to produce the Th-228-rich effluent (1100), and then recycled (1115) to the container (5000).

Figure 1H:
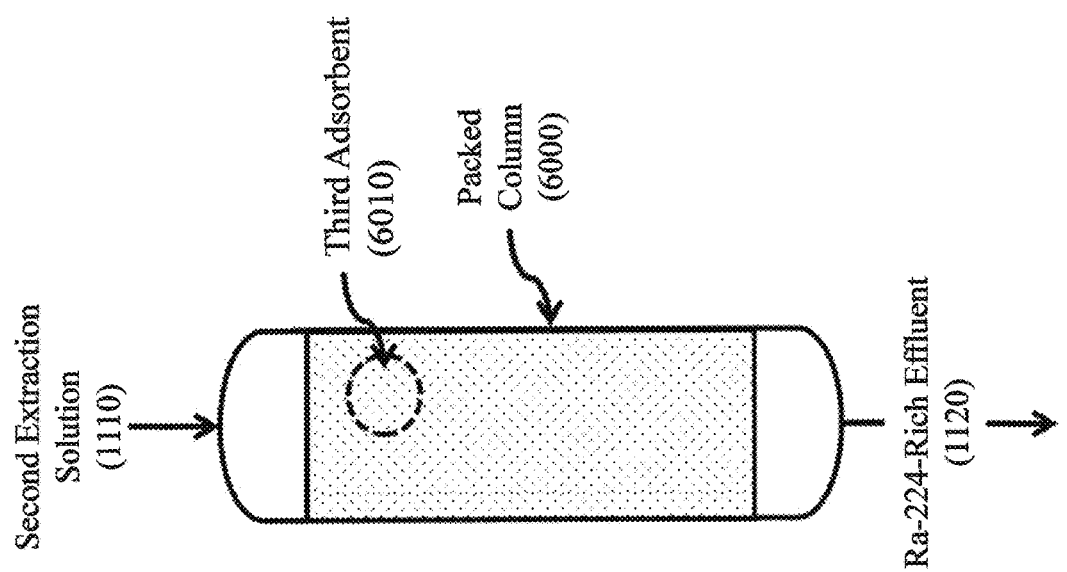
FIG. 1h is a schematic diagram of an embodiment for contacting an adsorbent with an extraction solution.

With reference now to FIG. 1h, the third adsorbent (6010) comprising the adsorbed Ra-224 cations may be contacted with a second extraction solution (1110). In this regard, the extraction solution is generally suitable for extracting at least some of the Ra-224 cations from the third adsorbent (6010). A Ra-224-rich effluent (1120) comprising at least some Ra-224 cations may be discharged from the packed column (6000) and recovered. The Ra-224-rich effluent (1120) comprising the Ra-224 cations may be a suitable product for generating Pb-212. As described in further detail below, Pb-212 may be useful in targeted alpha therapy cancer treatment therapies.

As noted above, Ra-228, Th-228, and Ra-224 may be useful products for generating Pb-212. Thus, any of the above product solutions described above comprising at least some of at least one or more of Ra-228, Th-228, and Ra-224 may be useful in generating Pb-212-containing solutions. A Pb-212-containing solution made therefrom may be suitable for use in a targeted alpha therapy cancer treatment therapy. For instance, the Pb-212 of the Pb-212-containing solution may be attached to an antibody and/or targeting molecule, which may subsequently be injected into a human.

Methods Utilizing U-233 as a Precursor

Figure 2A:
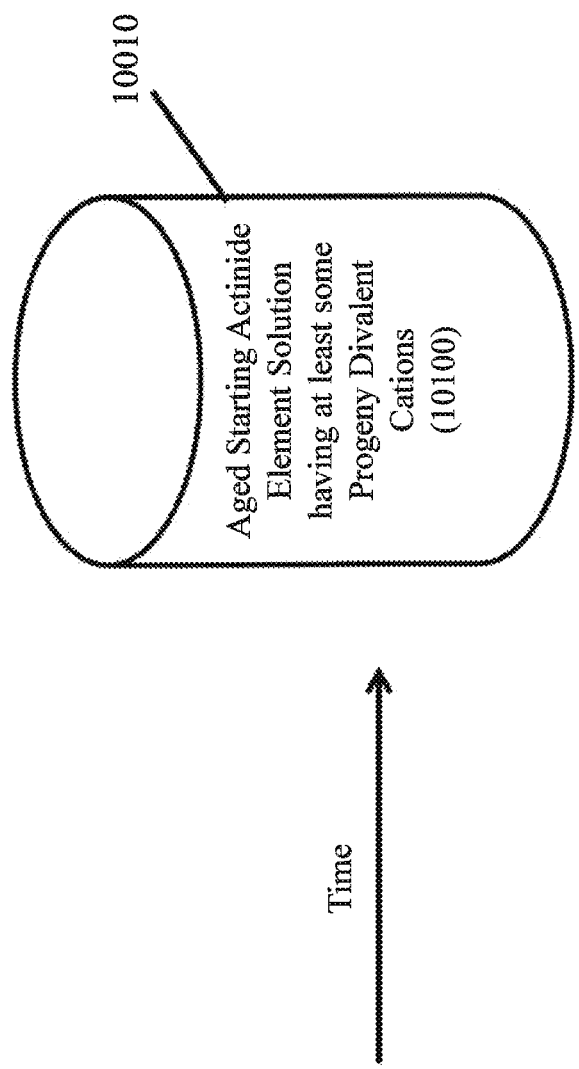
FIG. 2a is a schematic diagram of an embodiment for aging a starting actinide element solution having U-233 and/or Th-229 therein.
Figure 2A:
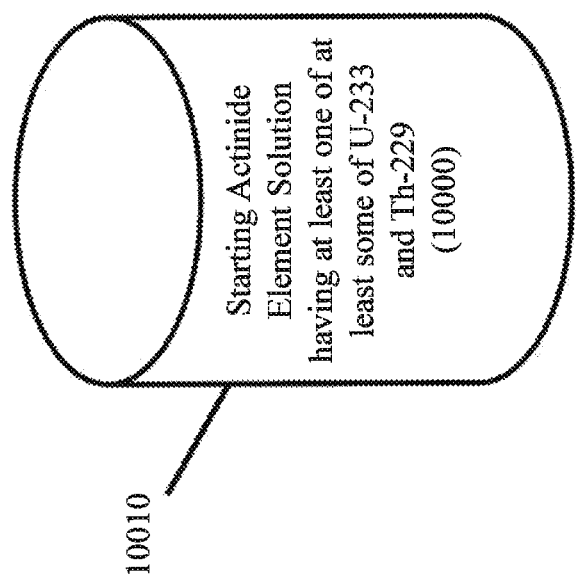

In another approach, and now with reference to FIG. 2a, U-233 and/or Th-229 may be used as a precursor for the production of one or more of the radioactive isotopes of Ac-225 and Ra-225. Such product solutions comprising one or more of Ac-225 and/or Ra-225 may be suitable for generating Bi-213, which may be useful in some targeted alpha therapy cancer treatment therapies. In this regard, a starting actinide element solution (10000) comprising at least some U-233 and/or Th-229, may be aged. Due to the aging (e.g., radioactive decay of U-233, Th-229, and/or progeny elements), an aged starting actinide element solution having progeny divalent cations (10100) may be produced. Progeny divalent cations produced via the radioactive decay chain of U-233 include Ra-225 and Pb-209. The starting actinide element solution (10000) and the subsequent aged starting actinide element solution (10100) may be held in a suitable container (10010), such as those described in greater detail below.

Figure 2B:
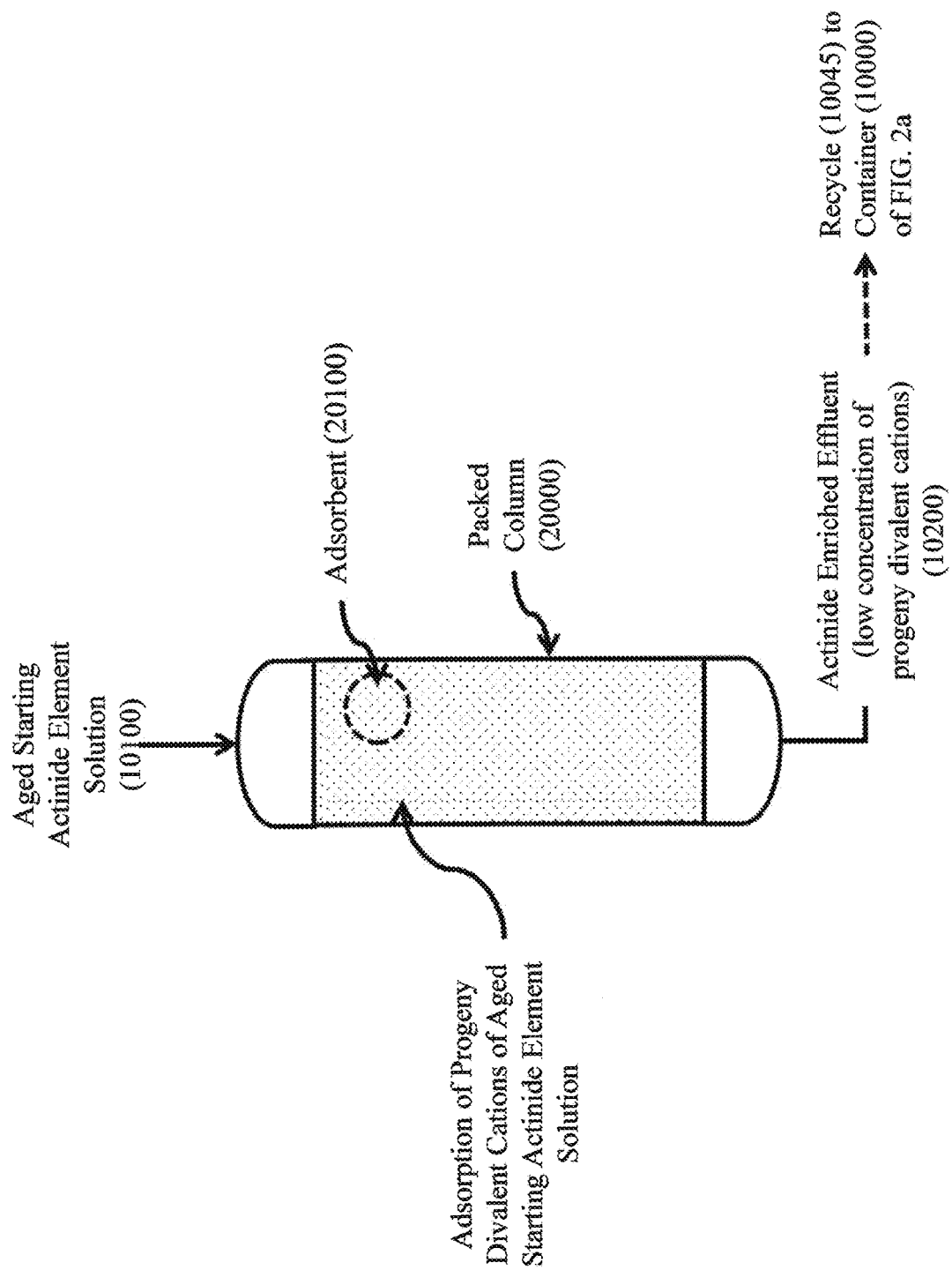
FIG. 2b is a schematic diagram of an embodiment for exposing an aged starting actinide element solution to an adsorbent.

With reference now to FIG. 2b, the aged starting actinide element solution (10100) may be exposed to an adsorbent (20100). In this regard, one suitable method for exposing the aged starting actinide element solution (10100) includes the use of a packed column (20000) comprising the adsorbent (20100), as illustrated. The adsorbent (20100) may have a selectivity towards divalent cations and, accordingly, may adsorb at least some progeny divalent cations (e.g., Ra-225 and/or Pb-209 cations) of the aged starting actinide element solution (10100). Suitable adsorbents (20100) having a selectivity towards divalent cations are discussed in greater detail below. Following exposure of the aged starting actinide element solution (10100) to the adsorbent (20100), an actinide enriched effluent (10200) may be discharged from the packed column (20000) and recovered. In one embodiment, the actinide enriched effluent (10200) may be recycled (10045) to the container (10010). In one embodiment, the actinide enriched effluent (10200) may itself be a starting actinide element solution (10000) to be aged to an aged starting actinide element solution (10100). The starting actinide element solution (10000) may be iteratively aged to an aged starting actinide element solution (10100), contacted with an adsorbent (20100), and recycled (10045). Due to the relative large half-life of U-233 of approximately 160,000 years, the process may be repeated indefinitely.

With reference now to FIG. 2c, the adsorbent (20100) may be contacted with an acidic wash solution (10300) to remove at least some of actinide elements from the adsorbent (20100). An acidic wash solution effluent comprising the acidic wash solution and at least some actinides (e.g., actinide element cations) (10400) may be discharged from the packed column (20000) and recovered. The acidic wash solution effluent may be recycled (10045) to the container (10010). In this regard, the recycled (10045) acidic wash effluent (10400) may be iteratively aged to produce progeny divalent cations and exposed to the adsorbent (20100) to adsorb the progeny divalent cations. Further, the acidic wash solution itself may be a starting actinide element solution (10000), or may be mixed with one or more starting actinide element solutions (10000). Similar to the process depicted by FIG. 2b, the process may be repeated indefinitely due to half-life of U-233.

Figure 2D:
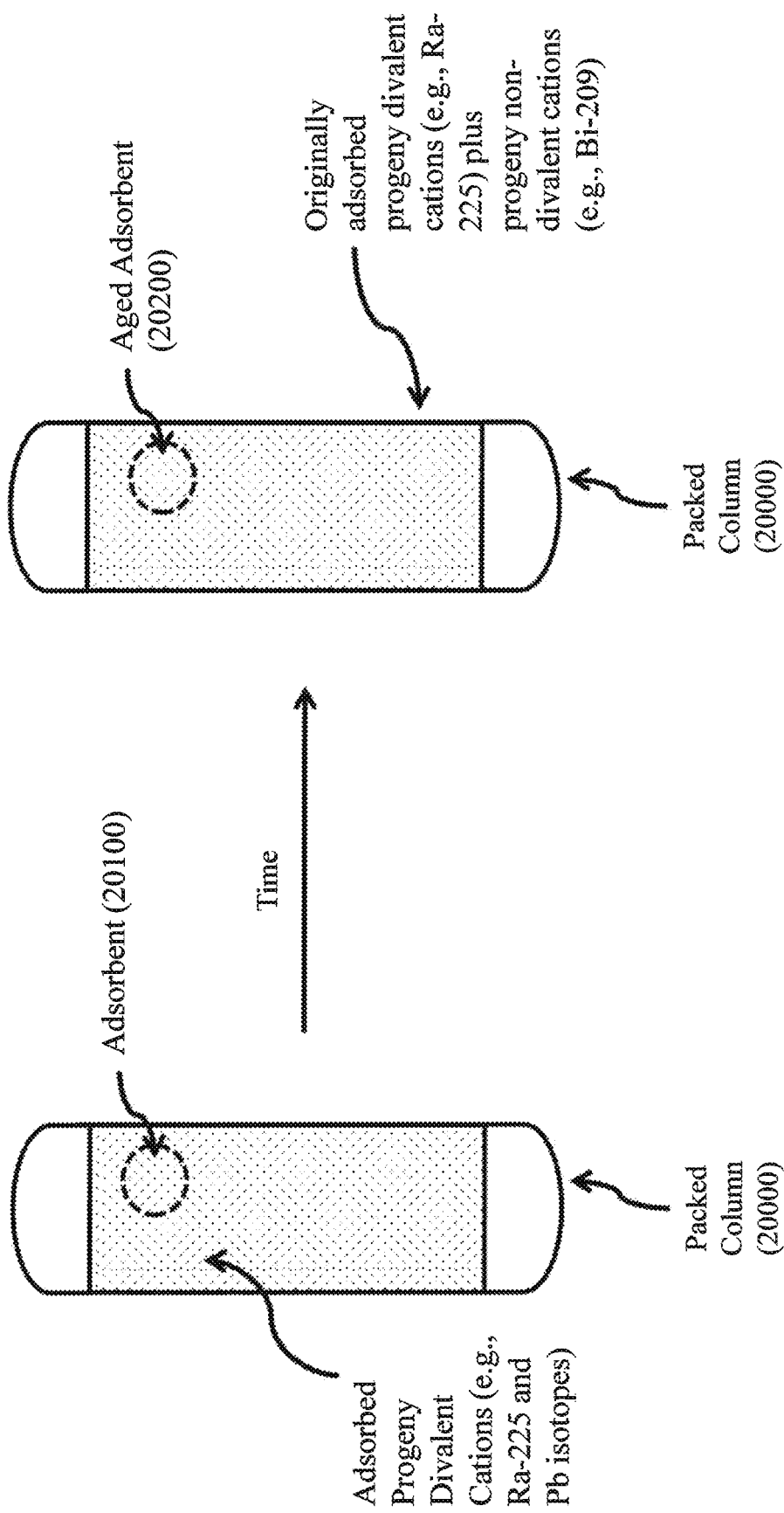
FIG. 2d is a schematic diagram of an embodiment for aging an adsorbent.

With reference now to FIG. 2d, after or during its contact with the extraction solution (1030) the adsorbent (20100) may be aged, where at least some of the absorbed progeny divalent cations (e.g. Ra-225; lead isotope(s) such as Pb-209) are aged to generate at least some of the progeny non-divalent cations. For instance, a short aging time (e.g., not greater than 24 hours) may be utilized such that a portion of the Pb-209 cations decay into non-divalent cations. For instance, a portion of the adsorbed Pb-209 may be allowed to decay due to its short half-life of approximately 3.3 hours. With an appropriate aging time, a large portion of Ra-225 cations will remain. Thus, the aged adsorbent (20200) generally comprises at least some adsorbed Ra-225 cations and at least some progeny non-divalent cations.

Figure 2E:
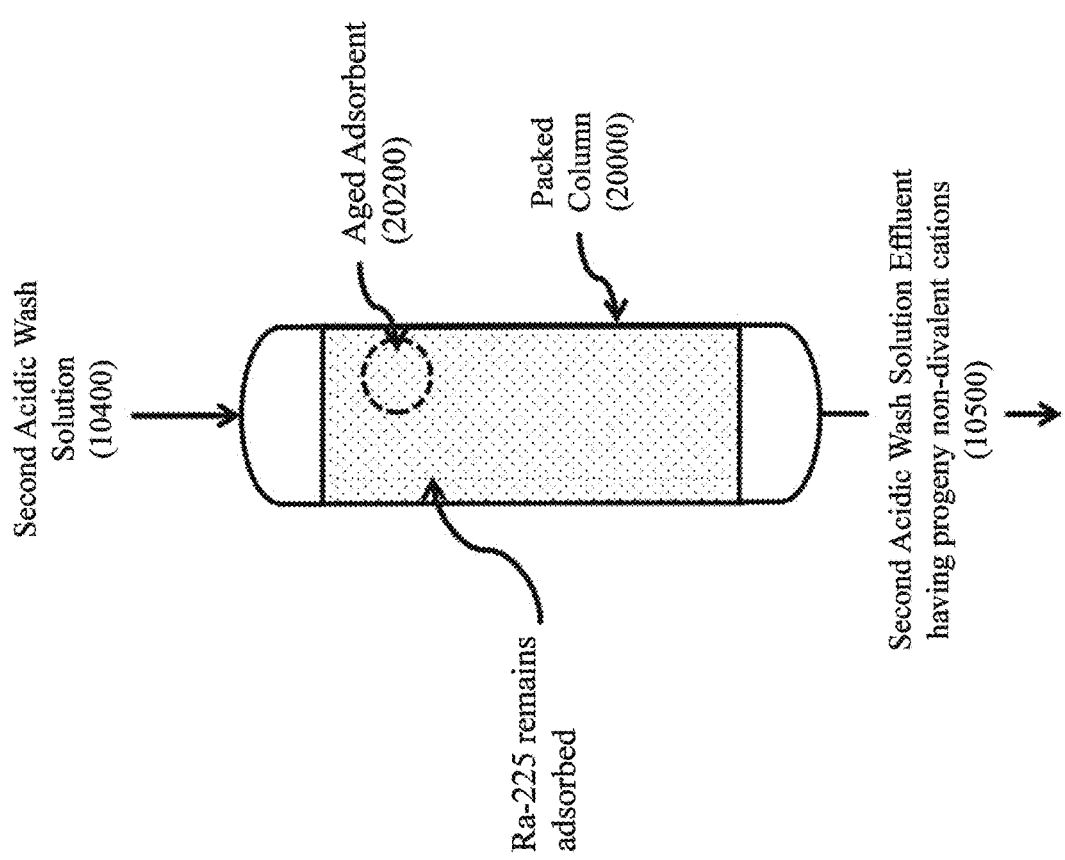
FIG. 2e is a schematic diagram of an embodiment for contacting an aged adsorbent with an acidic wash solution.

With reference now to FIG. 2e, the aged adsorbent (20200) may be contacted with a second acidic wash solution (10400). In this regard, contacting the aged adsorbent (20200) with the second acidic wash solution (10400) may remove at least some of the progeny non-divalent cations from the aged adsorbent (20200). A second acidic wash solution effluent having progeny non-divalent cations (10500) may be discharged from the column (20000) and recovered. Thus, after contacting the aged adsorbent (20200) with the second acidic wash solution (10400), the aged adsorbent (20200) may be enriched in Ra-225 cations and depleted in progeny non-divalent cations.

Figure 2F:
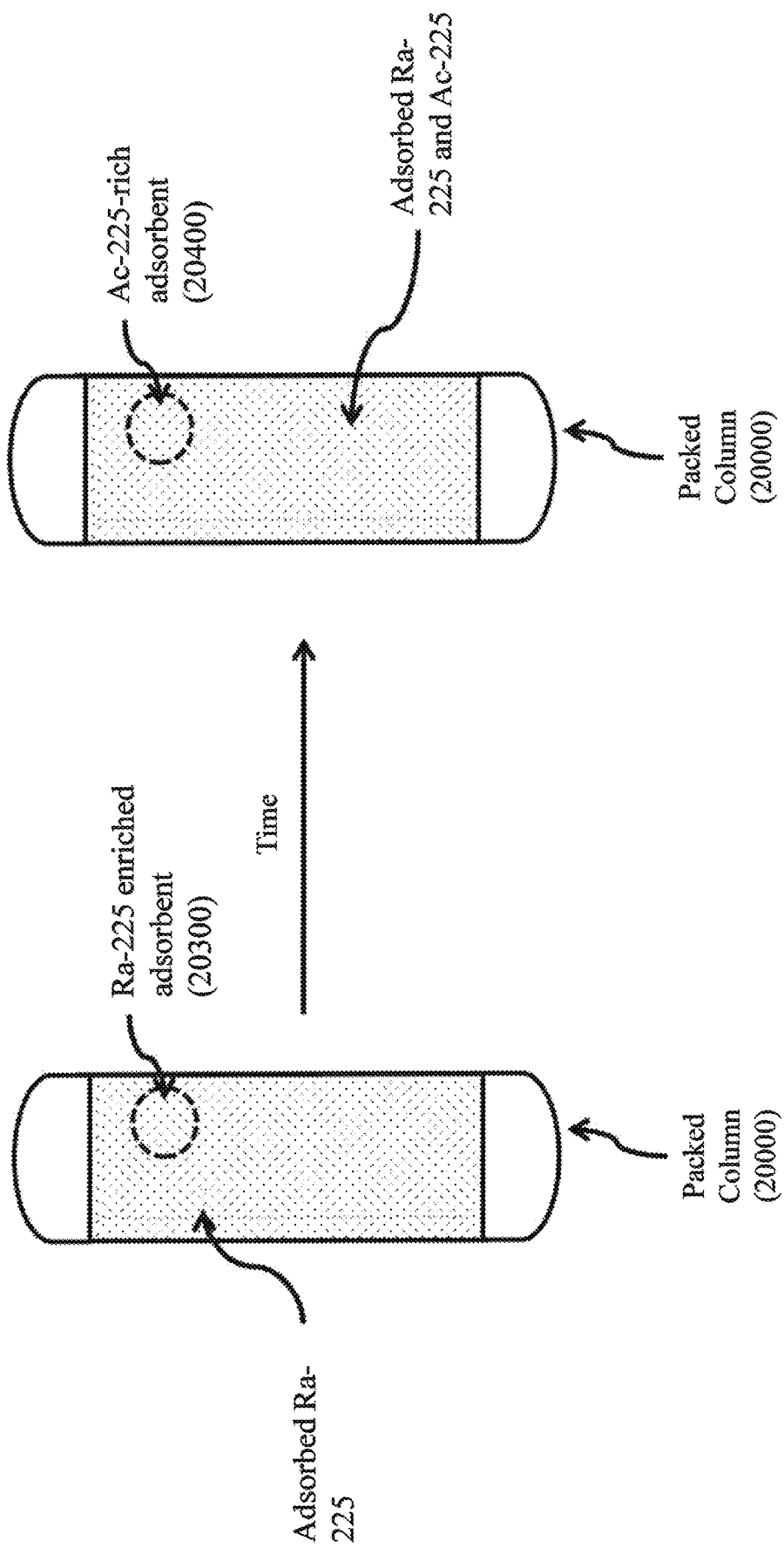
FIG. 2f is a schematic diagram of an embodiment for aging an Ra-225-rich adsorbent.

With reference to FIG. 2f, the Ra-225 enriched adsorbent (20300) may be aged such that the adsorbed Ra-225 cations may radioactively decay to Ac-225 cations. In some embodiments the aging occurs for at least one day (e.g., from one day to five days). Due to the aging, the Ra-225 enriched adsorbent (20300) may be transformed into an Ac-225 rich adsorbent (20400), having Ac-225 cations. Ac-225 cations are non-divalent cations, and therefore may be removed from the adsorbent using a suitable wash solution. In this regard, the Ac-225 cations may then be removed from the Ac-225-rich adsorbent via a third acidic wash solution. In this regard, and with reference now to FIG. 2g, the Ac-225-rich adsorbent (20400) may be contacted with a third acidic wash solution, and this contacting may transfer at least some of the Ac-255 cations from the Ac-225-rich adsorbent (20400) into the third acidic wash solution (10600). Thus, an acidic Ac-225-rich effluent (10700) comprising at least some of the acidic wash solution (10600) and at least some Ac-225 cations may be discharged from the packed column (20000) and recovered. The acidic Ac-225-rich effluent may be used to generate Bi-213 or Pb-209. Bi-213 and Pb-209 may be used in targeted alpha therapy cancer treatment therapies.

Figure 2G:
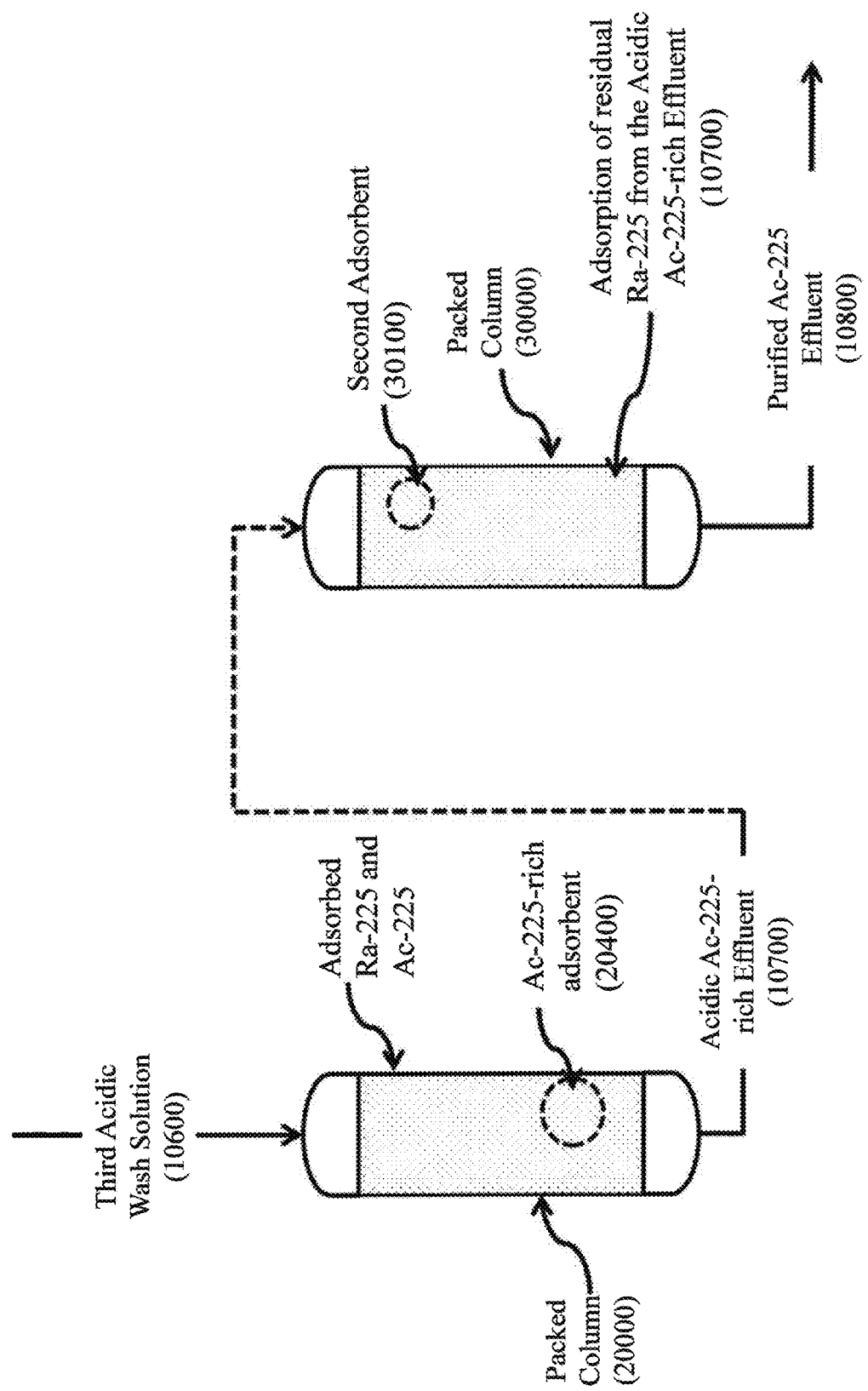
FIG. 2g is a schematic diagram of an embodiment for contacting an Ac-225-rich adsorbent with an acidic wash solution, recovering an acidic Ac-225-rich effluent, and optionally contacting the Ac-225-rich effluent with an adsorbent.

With continued reference to FIG. 2g, the acidic Ac-225-rich effluent (10700) may comprise residual Ra-225 cations. The acidic Ac-225-rich effluent may be purified by removing at least some of the residual Ra-225 cations, and a purified Ac-225 effluent (10800) may be recovered. One suitable method for purifying the acidic Ac-225-rich effluent comprises exposing the acidic Ac-225 rich effluent (10700) to a second adsorbent (30100), wherein the second adsorbent adsorbs at least some of the residual Ra-225 cations of a packed column (30000). In turn, a purified Ac-225 effluent (10800) may be discharged from the packed column (30000) and recovered. The purified Ac-225 effluent may be used in a targeted alpha therapy cancer treatment therapy. For instance, Ac-225 may decay via three alpha particle emissions to Bi-213, and may subsequently decay via a fourth alpha particle emission to Pb-209.

Figure 3A:
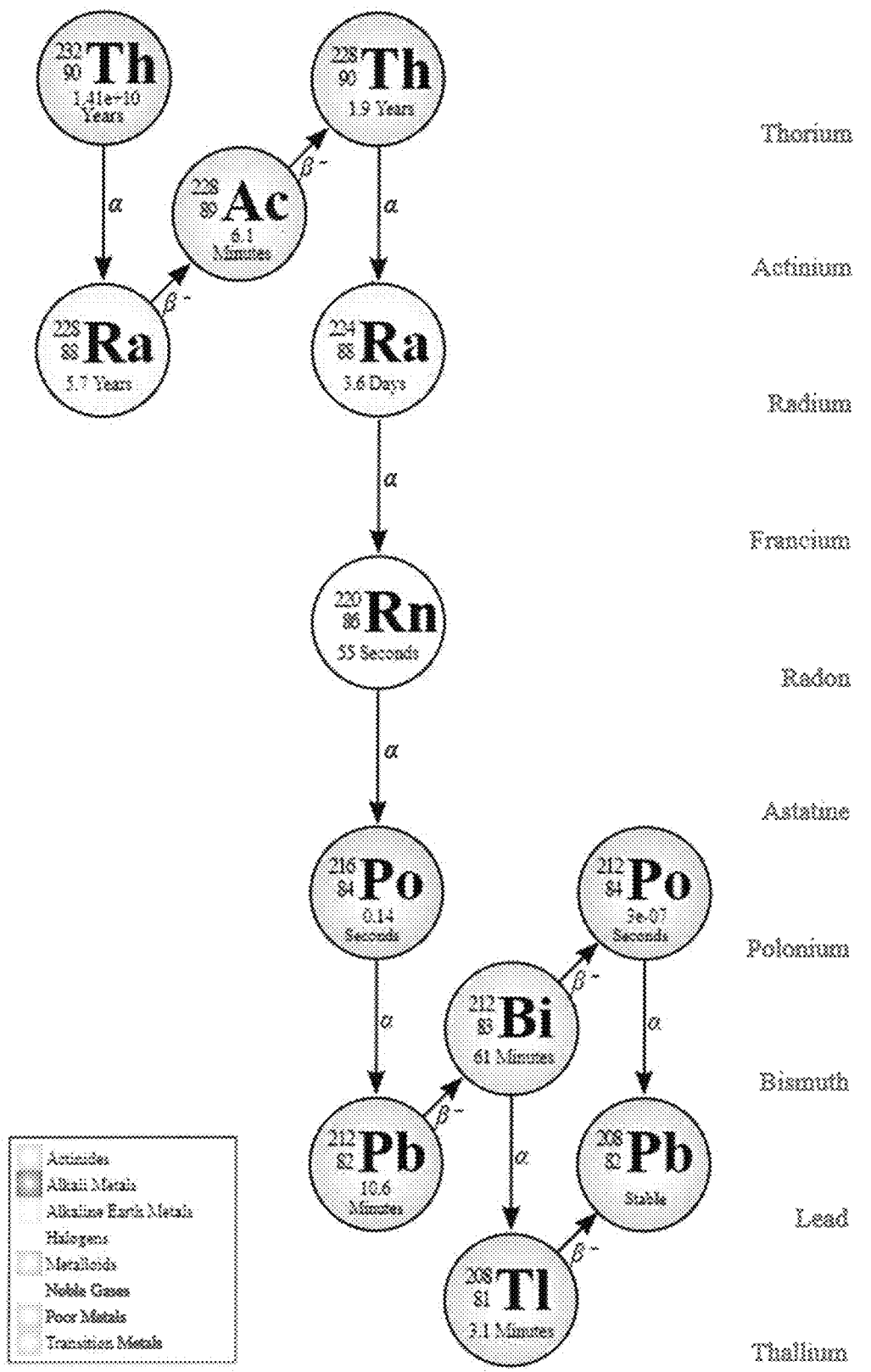
FIG. 3a is an illustration depicting the decay chain of Th-232.
Figure 3B:
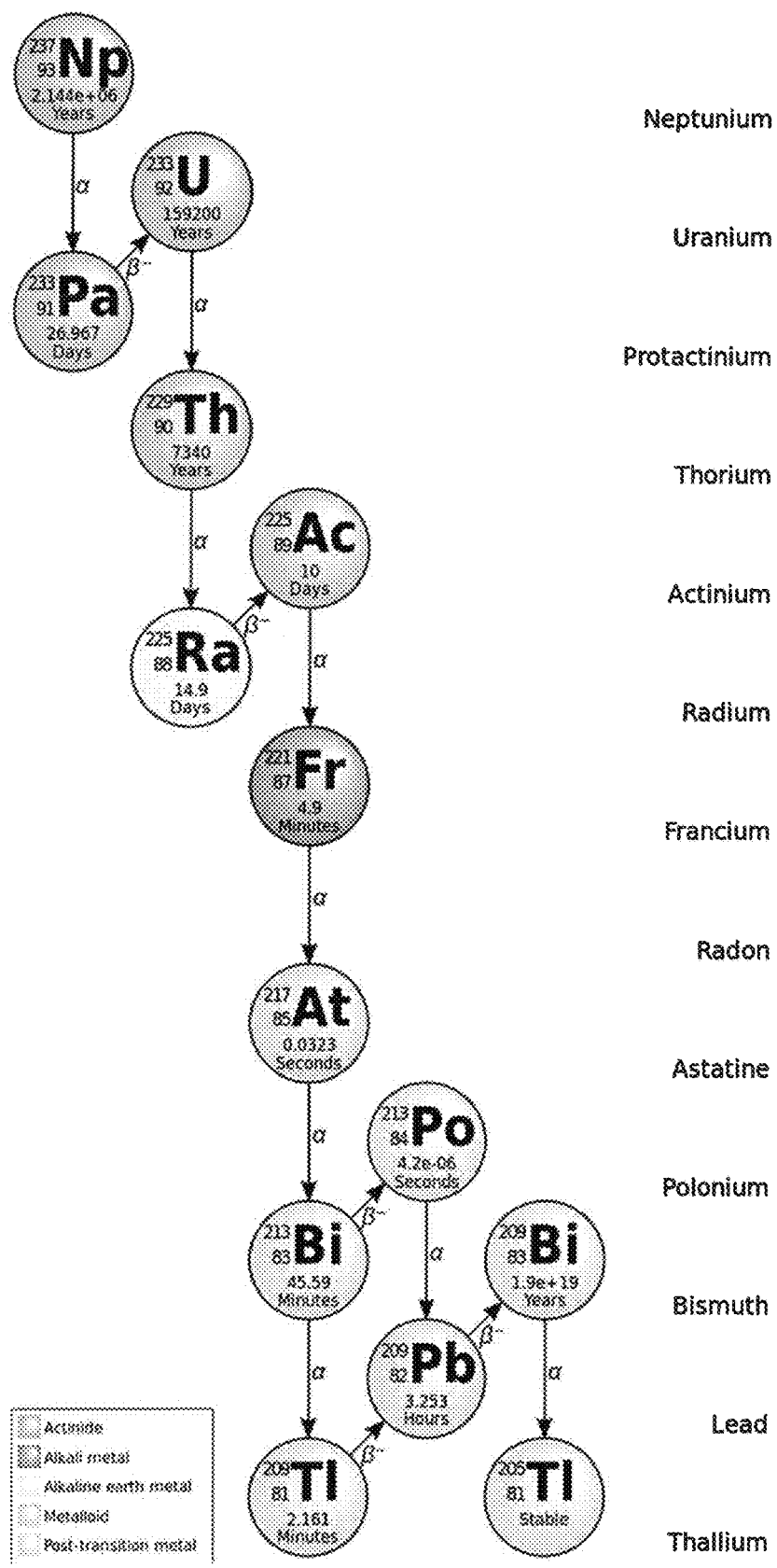
FIG. 3b is an illustration depicting the decay chain of U-233.

With reference now to FIGS. 3a and 3b, illustrations depicting the decay chain of the precursor materials described herein. In this regard, FIG. 3a illustrates the decay chain of Th-232. As shown, Th-232 decays via two beta emissions, and five alpha emissions to Pb-212. FIG. 3b illustrates the decay chain of U-233. As shown, natural precursors to U-233 that are illustrated are Np-237 and Pa-233. U-233 decays to Th-229 via alpha emission. As noted above, at least one of U-233 and Th-229 may be used as precursor materials. Further, U-233 decays via five alpha emissions and one beta emission to Bi-213.

ii. Systems

As noted above, various separation steps may be used to facilitate production of the radioactive isotope solutions described herein.

In one embodiment, one or more applicable containers are used (e.g., relative to various aging steps) in order to allow for the radioactive decay of one or more radioactive elements. See, e.g., containers 1000, 3000, and 5000 of FIGS. 1a, 1d, 1f, and container 10010 of FIG. 2a. In this regard, suitable materials for aging of and containment of the cation-containing solutions described herein may include glass (e.g., silica glass, borosilicate glass, etc.), and polymer materials. Some suitable polymer materials may include polymethylpentene, polyethylene, polyvinylchloride, polyvinylchloride free of plasticizing agents, and combinations thereof, among others.

In one embodiment, one or more applicable packed columns comprising the one or more adsorbents are used. See, e.g., packed columns 2000, 4000, and 6000 of FIGS. 1b, 1e, 1g-1h, and packed columns 20000, 30000 of FIGS. 2b-2g. In one embodiment, solutions may be provided to an inlet of the packed column and an effluent therefrom may be discharged from the outlet and collected. Suitable materials for the packed column include glass (e.g., silica glass, borosilicate glass, etc.), and polymer materials. Some suitable polymer materials may include polymethylpentene, polyethylene, polyvinylchloride, polyvinylchloride free of plasticizing agents, among others.

As noted above, adsorbents may be used to facilitate separations. In one embodiment, an adsorbent has a selectivity towards divalent cation elements. For instance, divalent cations of radium and/or lead may be selectively removed from one or more of the solutions described herein using a suitable adsorbent. In one embodiment, the adsorbents may comprise a stationary phase (e.g., a solid material that is insoluble in the solution being exposed). The stationary phase may comprise other materials tailored to facilitate the selective adsorption of divalent cations. The other materials may be tethered to the stationary phase (e.g., via covalently bonds), or otherwise incorporated into the stationary phase. In some embodiments, one or more of the adsorbents comprises one or more macrocyclic polyether materials. Such macrocyclic polyether materials may facilitate selective adsorption of divalent cations. In some embodiments, the one or more macrocyclic polyether materials comprise at least one crown ether, such as 18-crown-6 crown ether materials, and/or 21-crown-7 crown ether materials, among others. Further, various combinations of materials tailored to facilitate the selective adsorption of divalent cations may be used (e.g., combinations of crown ethers).

As noted above, the precursor material (APERI generator) may be at least one of Th-232, U-233 and Th-229. In this regard, the precursor material is generally dissolved in an acidic solution such to facilitate exposure to the adsorbents described herein. For instance, the Th-232, U-233, or Th-229 may be incorporated into a starting actinide element solution by dissolving a Th-232, U-233 or Th-229 material. Alternatively, a salt precursor of the actinide element (e.g., Th-232; U-233; Th-229) may be dissolved in aqueous solution. For instance, a thorium-232 salt, such as thorium nitrate may be a suitable precursor material. Salts of U-233 and Th-229 may also or alternatively be used. Suitable acids that may be used to dissolve the actinide elements include nitric acid, hydrofluoric acid, hydrochloric acid, sulfuric acid, and combinations thereof, among others. In the instance of salt precursor materials, the salt may comprise anions of these acidic materials (e.g., nitrate anions, fluoride anions, chloride anions, sulphate anions, and combinations thereof, among others). Furthermore, one or more of the acidic wash solutions described herein may be comprised of one or more of these acids.

As noted above, one or more extraction solutions may be used to extract progeny divalent cations from adsorbents. In this regard, the extraction solutions may comprise one or more extraction agents (e.g., agents capable of reacting with one or more of the progeny divalent cations). One suitable extraction agent is ethylenediaminetetraacetic acid ("EDTA"). EDTA may chelate the progeny divalent cations, thereby desorbing them from the adsorbent. Other suitable extraction agents include diammonium hydrogen citrate, diethylenetriaminepentaacetic acid (DTPA), and combinations thereof, among others. In one embodiment, the extraction solution comprises an extraction agent capable of chelating with divalent cations. In one embodiment, the extraction solution comprises at least EDTA. The concentration of one or more extraction agents may be sufficient to realize desorption of one or more of progeny divalent cations. The one or more extraction agents may be present in the extraction solution in an amount sufficient to facilitate desorption of divalent cations, but generally less than their solubility limit(s). The solubility of the extraction agents may be modified by pH modification. In one embodiment, an extraction solution comprises up to 0.25M EDTA.

ii. Products

As noted above, alpha particle emitting radioactive isotopes may be beneficial for use in TAT, and the methods described above may be useful in producing such alpha particle emitting radioactive isotopes. In one embodiment, a solution comprises a therapeutically effective amount of alpha particle emitting radioactive isotopes (e.g., Pb-212, Bi-213, Ac-225 or any other suitable alpha particle emitting radioactive isotopes capable of being used in a medical setting). The solution(s) may optionally comprise at least one generator of such alpha particle emitting radioactive isotopes. In another embodiment, a solution comprises a therapeutically effect amount of at least one generator (e.g., Ra-228, Th-228, Ra-224) of such alpha particle emitting radioactive isotopes. For purposes of simplicity, alpha particle emitting radioactive isotopes are called APERI herein, and generators of APERI (due to radioactive decay) are called APERI generators. The APERI generators may be, for instance, one or more of Ra-228, Ac-228, Th-228, Ra-224 in the case of Pb-212, or one or more of Ra-225 and Ac-225 in the case of Bi-213. The solution comprising the therapeutically effective amount of APERI, optionally with the APERI generators, may also include residual amounts of adsorbent(s) used during the production of the APERI generators. The adsorbent(s) may be any of the adsorbents described above (e.g., crown ethers). In one embodiment, the solution comprising the therapeutically effective amount of APERI, optionally with the APERI generators, includes at least 0.1 ppm or at least 0.5 ppm of adsorbent(s). In one embodiment, the adsorbent(s) comprise at least one crown ether material. In one embodiment, the solution comprising the therapeutically effective amount of APERI, optionally with the APERI generators, includes not greater than 1000 ppm or not greater than 500 ppm of the adsorbent(s).

As used herein, "a solution comprises a therapeutically effective amount of alpha particle emitting radioactive isotopes" means a solution includes an amount of the APERI sufficient to facilitate use in producing materials for use in a medical treatment, such as TAT treatment. In one embodiment, the solution comprising the therapeutically effective amount of APERI is used to produce a carrier having APERI attached thereto. In one embodiment, at least some of these carriers having the APERI attached thereto are injected into a human. A carrier is a compound that carries the APERI to the treatment region/area. In one embodiment, the carrier is an antibody. In another embodiment, the carrier is a targeting molecule. In one embodiment, Pb-212 is attached to the carrier. Other of the above identified APERI generators may be attached to a carrier and injected into a human.

While various embodiments of the present disclosure have been described in detail, it is apparent that modifications and adaptations of those embodiments will occur to those skilled in the art. However, it is to be expressly understood that such modifications and adaptations are within the spirit and scope of the present disclosure.

What is claimed is:

1. A method comprising:
   (a) aging a starting actinide element solution comprising Th-232 cations, wherein the aging comprises:
      (i) radioactively decaying at least some of the Th-232 cations, thereby producing an aged starting actinide element solution having at least some progeny divalent cations, wherein the progeny divalent cations include one or more of Ra-228, Ra-224, Pb-212, and Pb-208; and
   (b) flowing the aged starting actinide element solution through a column having an adsorbent, thereby adsorbing, by the adsorbent, at least some of the progeny divalent cations of the aged actinide element solution, wherein the adsorbent comprises at least one macrocyclic polyether material.

2. The method of claim 1, comprising:
   after the flowing, contacting the adsorbent with an extraction solution, thereby desorbing at least some of the progeny divalent cations from the adsorbent, wherein the extraction solution comprises a chelating agent; and
   recovering an extraction effluent solution, wherein the extraction effluent solution comprises at least some of the extraction solution and at least some progeny divalent cations, wherein at least 75% of the adsorbed progeny divalent cations are recovered in the extraction effluent solution.

3. The method of claim 2, comprising:
   aging the extraction effluent solution, wherein the aging the extraction effluent solution comprises:
      radioactively decaying at least some of the progeny divalent cations, thereby producing an aged extraction effluent solution comprising at least some Ac-228 cations and at least some Th-228 cations;
      wherein the aged extraction effluent solution comprises at least some of the progeny divalent cations.

4. The method of claim 3, wherein the adsorbent is a first adsorbent, the method comprising:
   exposing the aged extraction effluent solution to a second adsorbent, thereby removing at least some of the progeny divalent cations from the aged extraction effluent solution;
   wherein the exposing the aged extraction effluent solution to a second adsorbent comprises adsorbing, by the second adsorbent, at least some of the progeny divalent cations of the aged extraction effluent solution; and
   after the exposing, recovering a purified thorium effluent comprising the aged extraction effluent solution and at least some Th-228 cations.

5. The method of claim 4, comprising:
aging the purified thorium effluent, wherein the aging the purified thorium effluent comprises:
radioactively decaying at least some of the Th-228 cations, thereby producing an aged Ra-224-containing solution, wherein the aged Ra-224-containing solution comprises at least some Ra-224 cations; and
exposing the aged Ra-224-containing solution to a third adsorbent, thereby removing at least some of the Ra-224 cations from the aged Ra-224-containing solution;
wherein the exposing the Ra-224-containing solution to a third adsorbent comprises adsorbing, by the third adsorbent, at least some of the Ra-224 cations of the aged Ra-224-containing solution.

6. The method of claim 5, wherein the extraction solution is a first extraction solution, the method comprising:
after the exposing the aged Ra-224-containing solution, contacting the third adsorbent with a second extraction solution, thereby desorbing at least some of the Ra-224 cations from the third adsorbent; and
after the contacting the third adsorbent with the second extraction solution, recovering a Ra-224-rich effluent, wherein the Ra-224-rich effluent comprises the second extraction solution and at least some Ra-224 cations.

7. The method of claim 6, comprising generating a Pb-212-containing solution from at least one of (i) the aged extraction effluent solution having Th-228 cations, and (ii) the Ra-224-rich effluent, wherein the Pb-212-containing solution comprises at least some Pb-212 cations.

8. The method of claim 7, comprising attaching at least some of the Pb-212 cations to a carrier.

9. The method of claim 8, comprising injecting the carrier having the Pb-212 into a human.

10. A method comprising:
(a) aging a solution having divalent cations therein;
  (i) wherein the divalent cations comprise at least one of Ra-228 cations, Ra-224 cations, Pb-212 cations, and Pb-208 cations; and
  (ii) wherein the aging comprises radioactively decaying at least some of the divalent cations, thereby producing an aged solution comprising Ac-228 cations, Th-228 cations, and some of the divalent cations;
(b) flowing the aged solution through a column comprising an adsorbent, thereby removing at least some of the divalent cations from the aged solution, wherein the adsorbent comprises at least one macrocyclic polyether material; and
(c) recovering a purified thorium effluent, wherein the purified thorium effluent comprises the aged solution and at least some Th-228 cations.

11. A method comprising:
(a) aging a thorium-containing solution;
  (i) wherein the thorium-containing solution comprises at least some Th-228 cations; and
  (ii) wherein the aging the thorium-containing solution comprises radioactively decaying at least some of the Th-228 cations, thereby producing an aged solution comprising Ra-224 cations and some Th-228 cations;
(b) flowing the aged solution through a column comprising an adsorbent, thereby removing at least some of the Ra-224 cations from the aged solution, wherein the adsorbent comprises at least one macrocyclic polyether material;
(c) recovering a purified thorium effluent, wherein the purified thorium effluent comprises the aged solution and at least some Th-228 cations.

* * * * *